(12) United States Patent
Nettekoven et al.

(10) Patent No.: US 7,507,736 B2
(45) Date of Patent: Mar. 24, 2009

(54) INDOL-2-YL-PIPERAZIN-1-YL-METHANONE DERIVATIVES

(75) Inventors: Matthias Nettekoven, Grenzach-Wyhlen (DE); Jean-Marc Plancher, Hagenthal-le-Bas (FR); Hans Richter, Grenzach-Wyhlen (DE); Olivier Roche, Folgensbourg (FR); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/019,682

(22) Filed: Jan. 25, 2008

(65) Prior Publication Data

US 2008/0188484 A1 Aug. 7, 2008

(30) Foreign Application Priority Data

Feb. 7, 2007 (EP) .................................. 07101879

(51) Int. Cl.
*A61K 31/454* (2006.01)
*A61K 31/496* (2006.01)
*C07D 401/12* (2006.01)
*C07D 451/06* (2006.01)

(52) U.S. Cl. ............................ 514/253.04; 514/253.09; 544/362; 544/364; 544/121

(58) Field of Classification Search ................ None
See application file for complete search history.

(56) References Cited

U.S. PATENT DOCUMENTS

2004/0224952 A1 11/2004 Cowart et al.

FOREIGN PATENT DOCUMENTS

| WO | WO 01/51466 | 7/2001 |
| WO | WO 03/064413 | 8/2003 |
| WO | WO 2005/123716 | 12/2005 |
| WO | WO 2006/035308 | 4/2006 |
| WO | WO 2007/062999 | 6/2007 |
| WO | WO 2007/063000 | 6/2007 |

OTHER PUBLICATIONS

Masaki et al., Endocrinology, 144, pp. 2741-2748 (2003).
Hancock et al., European J. of Pharmacol., 487, pp. 183-197 (2004).
Timmermann, H., J. Med. Chem., 33, pp. 4-11 (1990).
Hino et al., Chem. Pharm. Bull, 38, pp. 59-64 (1990).
Skibo et al., J. Med. Chem., 44, pp. 3545-3562 (2001).
Ishii et al., Chem. Pharm. Bull., 22(9), pp. 1981-1989 (1974).
Scapecchi et al., Bioorg. Med. Chem., 12, pp. 71-85 (2004).
Hughes, D. L., the Mitsunobu Reaction. Organic Reactions (New York), 42, pp. 335-343 (1992).
Zaragoza et al., J. Med. Chem., 47, pp. 2833-2838 (2004).
Mederski et al., Tetrahedron, 55, pp. 12757-12770 (1999).
Leadbetter et al., J. Org. Chem., 39, pp. 3580-3583 (1974).

*Primary Examiner*—Emily Bernhardt
(74) *Attorney, Agent, or Firm*—George W. Johnston; Dennis P. Tramaloni; Brian C. Remy

(57) ABSTRACT

The present invention relates to compounds of formula I

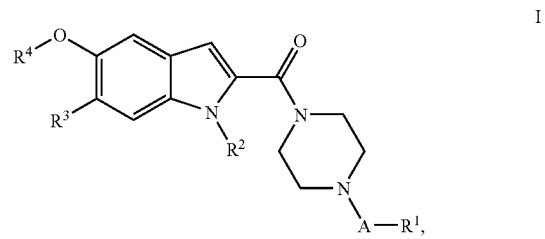

wherein A and $R^1$ to $R^4$ are as defined in the description and claims, and pharmaceutically acceptable salts thereof. The compounds are useful for the treatment and/or prevention of diseases which are associated with the modulation of H3 receptors.

22 Claims, No Drawings

INDOL-2-YL-PIPERAZIN-1-YL-METHANONE DERIVATIVES

PRIORITY TO RELATED APPLICATION(S)

This application claims the benefit of European Patent Application No. 07101879.0, filed Feb. 7, 2007, which is hereby incorporated by reference in its entirety.

BACKGROUND OF THE INVENTION

The present invention relates to novel (1H-indol-2-yl)-piperazin-1-yl-methanone derivatives, their manufacture, pharmaceutical compositions containing them and their use as medicaments. The active compounds of the present invention are antagonists and/or inverse agonists at the histamine 3 receptor (H3 receptor)

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tubero-mammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors. H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

It is therefore an object of the present invention to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

The invention is concerned with the compounds of formula (I):

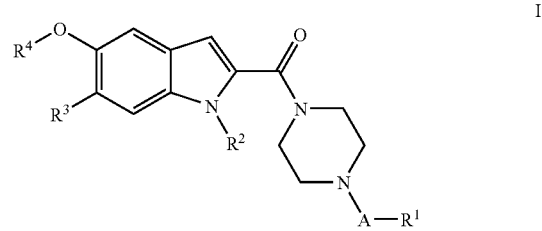

and pharmaceutically acceptable salts thereof, wherein A and $R^1$—$R^4$ are as defined in the detailed description and claims. In addition, the present invention relates to the methods of manufacturing and using the compounds of formula I as well as pharmaceutical compositions containing them. The compounds of formula I are antagonists and/or inverse agonists at the histamine 3 receptor (H3 receptor) and may be useful in treating obesity and other disorders associated with the H3 receptor.

DETAILED DESCRIPTION OF THE INVENTION

In the present description the term "alkyl", alone or in combination with other groups, refers to a branched or straight-chain monovalent saturated aliphatic hydrocarbon radical of one to twenty carbon atoms. In certain preferred embodiments, the alkyl group has one to sixteen carbon atoms, and more preferably one to ten carbon atoms.

The term "lower alkyl" or "$C_1$-$C_7$-alkyl", alone or in combination, signifies a straight-chain or branched-chain alkyl group with 1 to 7 carbon atoms. In certain preferred embodiments, the lower alkyl or $C_1$-$C_7$-alkyl group is a straight or branched-chain alkyl group with 1 to 6 carbon atoms and particularly preferred are straight or branched-chain alkyl groups with 1 to 4 carbon atoms. Examples of straight-chain and branched $C_1$-$C_7$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferably methyl.

The term "cycloalkyl" or "$C_3$-$C_7$-cycloalkyl" denotes a saturated carbocyclic group containing from 3 to 7 carbon atoms. Examples include cyclopropyl, cyclobutyl, cyclopentyl, cyclohexyl and cycloheptyl. Especially preferred are cyclobutyl and cyclopentyl.

The term "lower cycloalkylalkyl" or "$C_3$-$C_7$-cycloalkyl-$C_1$-$C_7$-alkyl" refers to lower alkyl groups as defined above wherein at least one of the hydrogen atoms of the lower alkyl group is replaced by cycloalkyl. A preferred example is cyclopropylmethyl.

The term "alkoxy" or "lower alkoxy" refers to the group R'—O—, wherein R' is lower alkyl and the term "lower alkyl" has the previously given significance. Examples of lower alkoxy groups are, for example, methoxy, ethoxy, n-propoxy, isopropoxy, n-butoxy, isobutoxy, sec.-butoxy and tert.-butoxy, preferably methoxy and ethoxy and most preferably ethoxy.

The term "lower hydroxyalkyl" or "hydroxy-$C_1$-$C_7$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "lower alkoxyalkyl" or "$C_1$-$C_7$-alkoxy-$C_1$-$C_7$-alkyl" refers to lower alkyl groups as defined above wherein at least one of the hydrogen atoms of the lower alkyl group is replaced by an alkoxy group. In certain preferred embodiments at least one of the hydrogen atoms of the lower alkyl group is replaced by methoxy or ethoxy. Among the preferred lower alkoxyalkyl groups are 2-methoxyethyl or 3-methoxypropyl.

The term "halogen" refers to fluorine, chlorine, bromine or iodine. In certain preferred embodiments the halogen is fluorine, chlorine or bromine.

The term "lower halogenalkyl" or "halogen-$C_1$-$C_7$-alkyl" refers to lower alkyl groups as defined above wherein at least one of the hydrogen atoms of the lower alkyl group is replaced by a halogen atom. In certain preferred embodiments at least one of the hydrogen atoms of the lower alkyl group is replaced by fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are methylsulfonyl and ethylsulfonyl.

The term "phenylsulfonyl" refers to the group R"—S(O)$_2$—, wherein R" is phenyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "lower phenylalkyl" or "phenyl-$C_1$-$C_7$-alkyl" refers to lower alkyl groups as defined above wherein at least one of the hydrogen atoms of the lower alkyl group is replaced by a phenyl group. Preferred lower phenylalkyl groups are benzyl and phenethyl.

The term "heteroaryl" in general refers to an aromatic 5- or 6-membered ring which can comprise one, two or three atoms independently selected from nitrogen, oxygen and sulphur (such as but not limited to furyl, pyridyl, 1,2-, 1,3- and 1,4-diazinyl, thienyl, isoxazolyl, oxazolyl, imidazolyl, and pyrrolyl). The term "heteroaryl" further refers to bicyclic aromatic groups comprising two 5- or 6-membered rings, in which one or both rings can contain one, two or three atoms independently selected from nitrogen, oxygen and sulphur (such as but not limited to indole or quinoline). A preferred heteroaryl group is pyridyl.

The term "form a 5- or 6-membered heterocyclic ring optionally containing a further heteroatom of nitrogen, oxygen or sulfur" refers to a N-heterocyclic ring, which may optionally contain a further nitrogen, oxygen or sulfur atom, such as (but not limited to) pyrrolidinyl, imidazolyl, oxazolidinyl, isoxazolidinyl, thiazolidinyl, isothiazolidinyl, piperidinyl, pyrazinyl, morpholinyl and thiomorpholinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared from the addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space and have one or more asymmetric carbon atoms are termed "stereoisomers". Stereoisomers that are not mirror images of one another are termed "diastereoisomers", and stereoisomers that are non-superimposable mirror images are termed "enantiomers", or sometimes optical isomers.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to the compounds of formula I:

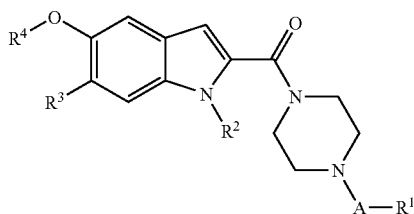

and any pharmaceutically acceptable salts thereof, wherein:
A is C(O) or S(O)$_2$;
$R^1$ is selected from the group consisting of:
(1) lower alkyl,
(2) lower alkoxy,
(3) cycloalkyl,
(4) lower cycloalkylalkyl,
(5) lower halogenalkyl,
(6) phenyl unsubstituted or substituted with one to three substituents independently selected from the group consisting of lower alkyl, lower alkoxy, halogen, lower halogenalkyl and cyano,
(7) lower phenylalkyl wherein the phenyl ring may be unsubstituted or substituted with one to three substituents independently selected from the group consisting of lower alkyl, lower alkoxy, halogen, lower halogenalkyl and cyano, and
(8) —NR$^5$R$^6$, wherein R$^5$ and R$^6$ independently from each other are selected from the group consisting of lower alkyl, cycloalkyl, lower cycloalkylalkyl, lower halogenalkyl and lower phenylalkyl, or alternatively, R$^5$ and R$^6$ together with the nitrogen atom to which they are attached form a 5- or 6-membered heterocyclic ring optionally containing a further heteroatom of nitrogen, oxygen or sulfur;
$R^2$ is selected from the group consisting of:
(1) hydrogen,
(2) lower alkyl,
(3) cycloalkyl,
(4) lower cycloalkylalkyl,
(5) lower hydroxyalkyl,
(6) lower alkoxyalkyl,
(7) lower halogenalkyl,
(8) lower cyanoalkyl,
(9) lower alkylsulfonyl,
(10) lower alkanoyl,
(11) phenylsulfonyl wherein the phenyl ring may be unsubstituted or substituted with one to three substitutents independently selected from the group consisting of lower alkyl, halogen, lower alkoxy, lower halogenalkoxy and lower hydroxyalkyl,
(12) phenyl unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino,
(13) benzodioxolyl,
(14) lower phenylalkyl, wherein the phenyl ring may be unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
(15) heteroaryl unsubstituted or substituted with one or two substituents independently selected from the group consisting of lower alkyl, lower alkoxy, cyano, morpholinyl and halogen;
$R^3$ is hydrogen, halogen or methyl; and
$R^4$ is either $R^{4a}$ or $R^{4b}$:

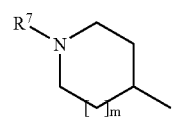

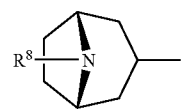

wherein:
m is 0 or 1;
$R^7$ is lower alkyl, cycloalkyl, or lower halogenalkyl; and
$R^8$ is lower alkyl, cycloalkyl, or lower halogenalkyl.

Preferred are compounds of formula I according to the present invention, wherein A is S(O)$_2$, meaning compounds of formula I having the formula

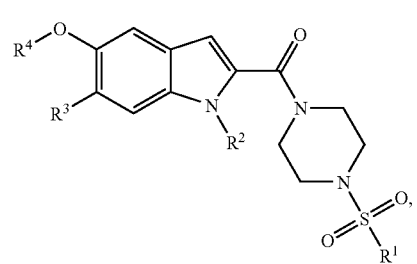

wherein $R^1$, $R^2$, $R^3$ and $R^4$ are as defined herein before, and pharmaceutically acceptable salts thereof.

Also preferred are compounds of formula I according to the present invention, wherein A is C(O), meaning compounds of formula I having the formula

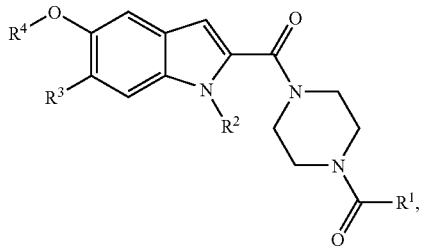

I-ii wherein R¹, R², R³ and R⁴ are as defined herein before, and pharmaceutically acceptable salts thereof.

Further preferred are the compounds of formula I according to the present invention, wherein R¹ is selected from the group consisting of lower alkyl, lower alkoxy,
cycloalkyl, lower cycloalkylalkyl,
lower halogenalkyl,
phenyl unsubstituted or substituted with one to three groups independently selected from lower alkyl, lower alkoxy, halogen, lower halogenalkyl and cyano, and
lower phenylalkyl wherein the phenyl ring may be unsubstituted or substituted with one to three groups independently selected from lower alkyl, lower alkoxy, halogen, lower halogenalkyl and cyano.

More preferred are the compounds of formula I, wherein R¹ is selected from the group consisting of lower alkyl, cycloalkyl, lower cycloalkylalkyl and lower halogenalkyl.

Also especially preferred are compounds of formula I according to the invention, wherein R¹ is phenyl unsubstituted or substituted with one to three groups independently selected from lower alkyl, lower alkoxy, halogen, lower halogenalkyl and cyano, or lower phenylalkyl wherein the phenyl ring may be unsubstituted or substituted with one to three groups independently selected from lower alkyl, lower alkoxy, halogen, lower halogenalkyl and cyano.

Compounds of formula I according to the invention are especially preferred, wherein R¹ is —NR⁵R⁶, wherein R⁵ and R⁶ independently from each other are selected from lower alkyl, cycloalkyl, lower cycloalkylalkyl, lower halogenalkyl and lower phenylalkyl, or wherein R⁵ and R⁶ together with the nitrogen atom to which they are attached form a 5- or 6-membered heterocyclic ring optionally containing a further heteroatom selected from nitrogen, oxygen or sulfur, said heterocyclic ring preferably being piperidine.

Especially preferred are also compounds of formula I, wherein A is C(O) and R¹ is lower alkoxy.

Also preferred are compounds of formula I according to the present invention, wherein R² is selected from the group consisting of hydrogen, lower alkyl, cycloalkyl, lower cycloalkylalkyl, lower hydroxyalkyl, lower alkoxyalkyl, lower halogenalkyl, lower cyanoalkyl, and pyridyl which is unsubstituted or substituted with one or two groups independently selected from lower alkyl, lower alkoxy, cyano, morpholinyl and halogen.

More preferred are compounds of formula I, wherein R² is hydrogen.

Especially preferred are compounds of formula I, wherein R² is lower alkyl.

Also more preferred are compounds of formula I, wherein R² is lower hydroxyalkyl or lower halogenalkyl.

Especially preferred are also compounds of formula I according to the invention, wherein R² is pyridyl which is unsubstituted or substituted with one or two groups independently selected from lower alkyl, lower alkoxy, cyano, morpholinyl and halogen.

Preferred compounds of formula I according to the invention are further those, wherein R³ is halogen or methyl, with those being more preferred, wherein R³ is halogen, and with those, wherein R³ is bromo or chloro, being most preferred.

Further preferred compounds of formula I include those, wherein R⁴ is

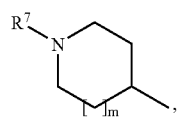

R⁴ᵃ wherein R⁷ is selected from the group consisting of lower alkyl, cycloalkyl and lower halogenalkyl and m is 0 or 1.

This means, compounds of formula I having the formula

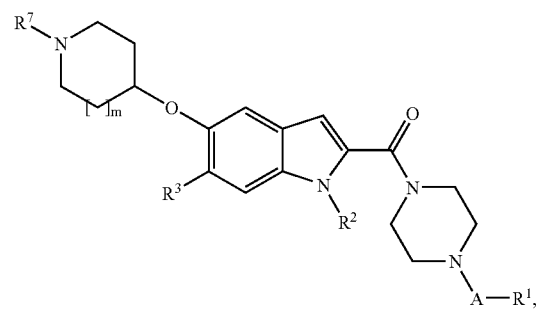

I-iii wherein A, R¹, R², R³, R⁷ and m are defined herein before, and pharmaceutically acceptable salts thereof, are preferred.

More preferably, R⁷ is isopropyl or 2,2,2-trifluoroethyl, and most preferably, R⁷ is isopropyl. Preferably, m is 1.

In addition, compounds of formula I according to the invention are preferred, wherein R⁴ is

R⁴ᵇ wherein $R^8$ is lower alkyl, meaning these are compounds of formula I having the formula

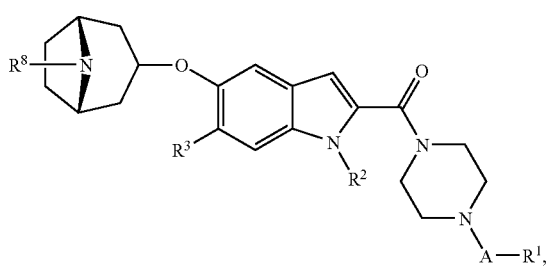

I-iv wherein A, $R^1$, $R^2$, $R^3$ and $R^8$ are as defined herein before, and pharmaceutically acceptable salts thereof.

Most preferably, $R^8$ is isopropyl.

Preferred compounds of formula I of the present invention are the following:

[6-bromo-5-(1-isopropyl-piperidin-4-yloxy)-1H-indol-2-yl]-[4-(piperidine-1-sulfonyl)-piperazin-1-yl]-methanone,
[6-bromo-5-(1-isopropyl-piperidin-4-yloxy)-1H-indol-2-yl]-(4-methanesulfonyl-piperazin-1-yl)-methanone,
4-[6-bromo-5-(1-isopropyl-piperidin-4-yloxy)-1H-indole-2-carbonyl]-piperazine-1-sulfonic acid dimethylamide,
[6-bromo-1-isopropyl-5-(1-isopropyl-piperidin-4-yloxy)-1H-indol-2-yl]-[4-(piperidine-1-sulfonyl)-piperazin-1-yl]-methanone,
[6-bromo-1-isopropyl-5-(1-isopropyl-piperidin-4-yloxy)-1H-indol-2-yl]-(4-methanesulfonyl-piperazin-1-yl)-methanone,
4-[6-bromo-1-isopropyl-5-(1-isopropyl-piperidin-4-yloxy)-1H-indole-2-carbonyl]-piperazine-1-sulfonic acid dimethylamide,
[6-bromo-1-(2-chloro-pyridin-4-yl)-5-(1-isopropyl-piperidin-4-yloxy)-1H-indol-2-yl]-[4-(piperidine-1-sulfonyl)-piperazin-1-yl]-methanone,
[6-bromo-1-(2-chloro-pyridin-4-yl)-5-(1-isopropyl-piperidin-4-yloxy)-1H-indol-2-yl]-(4-methanesulfonyl-piperazin-1-yl)-methanone,
4-[6-bromo-1-(2-chloro-pyridin-4-yl)-5-(1-isopropyl-piperidin-4-yloxy)-1H-indole-2-carbonyl]-piperazine-1-sulfonic acid dimethylamide,
[6-bromo-5-(1-isopropyl-piperidin-4-yloxy)-1H-indol-2-yl]-(4-ethanesulfonyl-piperazin-1-yl)-methanone,
[6-bromo-1-isopropyl-5-(1-isopropyl-piperidin-4-yloxy)-1H-indol-2-yl]-(4-ethanesulfonyl-piperazin-1-yl)-methanone,
[6-bromo-5-(1-isopropyl-piperidin-4-yloxy)-1-(2,2,2-trifluoro-ethyl)-1H-indol-2-yl]-(4-ethanesulfonyl-piperazin-1-yl)-methanone,
[6-bromo-5-(1-isopropyl-piperidin-4-yloxy)-1H-indol-2-yl]-[4-(propane-2-sulfonyl)-piperazin-1-yl]-methanone,
[6-bromo-5-(1-isopropyl-piperidin-4-yloxy)-1H-indol-2-yl]-[4-(propane-2-sulfonyl)-piperazin-1-yl]-methanone,
[6-bromo-1-isopropyl-5-(1-isopropyl-piperidin-4-yloxy)-1H-indol-2-yl]-[4-(propane-2-sulfonyl)-piperazin-1-yl]-methanone,
[6-bromo-1-isopropyl-5-(1-isopropyl-piperidin-4-yloxy)-1H-indol-2-yl]-(4-trifluoromethanesulfonyl-piperazin-1-yl)-methanone,
[6-bromo-5-(1-isopropyl-piperidin-4-yloxy)-1H-indol-2-yl]-(4-cyclopropanesulfonyl-piperazin-1-yl)-methanone,
[6-bromo-5-(1-isopropyl-piperidin-4-yloxy)-1H-indol-2-yl]-(4-cyclopropanecarbonyl-piperazin-1-yl)-methanone,
1-{4-[6-bromo-5-(1-isopropyl-piperidin-4-yloxy)-1H-indole-2-carbonyl]-piperazin-1-yl}-ethanone,
[6-bromo-1-(2-chloro-pyridin-4-yl)-5-(1-isopropyl-piperidin-4-yloxy)-1H-indol-2-yl]-(4-cyclopropanesulfonyl-piperazin-1-yl)-methanone,
[6-bromo-1-(2-chloro-pyridin-4-yl)-5-(1-isopropyl-piperidin-4-yloxy)-1H-indol-2-yl]-(4-cyclopropanecarbonyl-piperazin-1-yl)-methanone,
[6-bromo-1-isopropyl-5-(1-isopropyl-piperidin-4-yloxy)-1H-indol-2-yl]-(4-cyclopropanesulfonyl-piperazin-1-yl)-methanone,
[6-bromo-1-isopropyl-5-(1-isopropyl-piperidin-4-yloxy)-1H-indol-2-yl]-(4-cyclopropanecarbonyl-piperazin-1-yl)-methanone,
[6-bromo-1-(2-hydroxy-ethyl)-5-(1-isopropyl-piperidin-4-yloxy)-1H-indol-2-yl]-(4-cyclopropanesulfonyl-piperazin-1-yl)-methanone,
[6-bromo-1-(2-hydroxy-ethyl)-5-(1-isopropyl-piperidin-4-yloxy)-1H-indol-2-yl]-(4-cyclopropanecarbonyl-piperazin-1-yl)-methanone,
1-{4-[6-bromo-1-(2-hydroxy-ethyl)-5-(1-isopropyl-piperidin-4-yloxy)-1H-indole-2-carbonyl]-piperazin-1-yl}-ethanone,
1-{4-[6-bromo-1-isopropyl-5-(1-isopropyl-piperidin-4-yloxy)-1H-indole-2-carbonyl]-piperazin-1-yl}-ethanone,
1-{4-[6-bromo-1-(2-chloro-pyridin-4-yl)-5-(1-isopropyl-piperidin-4-yloxy)-1H-indole-2-carbonyl]-piperazin-1-yl}-ethanone,
[5-(1-isopropyl-piperidin-4-yloxy)-6-methyl-1H-indol-2-yl]-(4-methanesulfonyl-piperazin-1-yl)-methanone,
4-[5-(1-isopropyl-piperidin-4-yloxy)-6-methyl-1H-indole-2-carbonyl]-piperazine-1-carboxylic acid ethyl ester,
(4-cyclopropanecarbonyl-piperazin-1-yl)-[5-(1-isopropyl-piperidin-4-yloxy)-6-methyl-1H-indol-2-yl]-methanone,
[1-isopropyl-5-(1-isopropyl-piperidin-4-yloxy)-6-methyl-1H-indol-2-yl]-(4-methanesulfonyl-piperazin-1-yl)-methanone,
(4-cyclopropanecarbonyl-piperazin-1-yl)-[1-isopropyl-5-(1-isopropyl-piperidin-4-yloxy)-6-methyl-1H-indol-2-yl]-methanone,
4-[1-isopropyl-5-(1-isopropyl-piperidin-4-yloxy)-6-methyl-1H-indole-2-carbonyl]-piperazine-1-carboxylic acid ethyl ester,
4-[6-chloro-5-(1-isopropyl-piperidin-4-yloxy)-1#H!-indole-2-carbonyl]-piperazine-1-carboxylic acid-tert-butyl ester,
[6-chloro-5-(1-isopropyl-piperidin-4-yloxy)-1H-indol-2-yl]-piperazin-1-yl-methanone,
[6-chloro-5-(1-isopropyl-piperidin-4-yloxy)-1H-indol-2-yl]-(4-cyclopropanecarbonyl-piperazin-1-yl)-methanone
4-[6-chloro-5-(1-isopropyl-piperidin-4-yloxy)-1H-indole-2-carbonyl]-piperazine-1-carboxylic acid dimethylamide,
[6-chloro-5-(1-isopropyl-piperidin-4-yloxy)-1H-indol-2-yl]-(4-methanesulfonyl-piperazin-1-yl)-methanone,
[1-isopropyl-5-((1S,3R,5R)-8-isopropyl-8-aza-bicyclo[3.2.1]oct-3-yloxy)-1H-indol-2-yl]-[4-4-trifluoromethyl-benzenesulfonyl)-piperazin-1-yl]-methanone,
(4-benzenesulfonyl-piperazin-1-yl)-[1-isopropyl-5-((1S,3r,5R)-8-isopropyl-8-aza-bicyclo[3.2.1]oct-3-yloxy)-1H-indol-2-yl]-methanone,
[1-isopropyl-5-((1S,3R,5R)-8-isopropyl-8-aza-bicyclo[3.2.1]oct-3-yloxy)-1H-indol-2-yl]-[4-(propane-2-sulfonyl)-piperazin-1-yl]-methanone,
(4-ethanesulfonyl-piperazin-1-yl)-[1-isopropyl-5-((1S,3R,5R)-8-isopropyl-8-aza-bicyclo[3.2.1]oct-3-yloxy)-1H-indol-2-yl]-methanone,

[1-isopropyl-5-((1S,3R,5R)-8-isopropyl-8-aza-bicyclo[3.2.1]oct-3-yloxy)-1H-indol-2-yl]-[4-(toluene-4-sulfonyl)-piperazin-1-yl]-methanone,

[4-(4-chloro-benzenesulfonyl)-piperazin-1-yl]-[5-((1S,3R,5R)-8-isopropyl-8-aza-bicyclo[3.2.1]oct-3-yloxy)-1H-indol-2-yl]-methanone,

[1-isopropyl-5-((1S,3R,5R)-8-isopropyl-8-aza-bicyclo[3.2.1]oct-3-yloxy)-1H-indol-2-yl]-[4-(4-methoxy-benzenesulfonyl)-piperazin-1-yl]-methanone,

[1-isopropyl-5-((1S,3R,5R)-8-isopropyl-8-aza-bicyclo[3.2.1]oct-3-yloxy)-1H-indol-2-yl]-(4-phenylmethanesulfonyl-piperazin-1-yl)-methanone, 4-{4-[1-isopropyl-5-((1S,3R,5R)-8-isopropyl-8-aza-bicyclo[3.2.1]oct-3-yloxy)-1H-indole-2-carbonyl]-piperazine-1-sulfonyl}-benzonitrile,

[1-(2,2-difluoro-ethyl)-5-((1S,3R,5R)-8-isopropyl-8-aza-bicyclo[3.2.1]oct-3-yloxy)-1H-indol-2-yl]-(4-methanesulfonyl-piperazin-1-yl)-methanone, 4-[5-(1-isopropyl-piperidin-4-yloxy)-1H-indol-2-carbonyl]-piperazine-1-carboxylic acid-tert-butyl ester,

[5-(1-isopropyl-piperidin-4-yloxy)-1H-indol-2-yl]-piperazin-1-yl-methanone dihydrochloride,

[5-(1-isopropyl-piperidin-4-yloxy)-1H-indol-2-yl]-(4-methanesulfonyl-piperazin-1-yl)-methanone, 4-[1-isopropyl-5-(1-isopropyl-piperidin-4-yloxy)-1H-indole-2-carbonyl]-piperazine-1-carboxylic acid tert-butyl ester,

[1-isopropyl-5-(1-isopropyl-piperidin-4-yloxy)-1H-indol-2-yl]-piperazin-1-yl-methanone hydrochloride,

[1-isopropyl-5-(1-isopropyl-piperidin-4-yloxy)-1H-indol-2-yl]-(4-methanesulfonyl-piperazin-1-yl)-methanone, 4-[1-(2,2-difluoro-ethyl)-5-(1-isopropyl-piperidin-4-yloxy)-1H-indole-2-carbonyl]-piperazine-1-carboxylic acid tert-butyl ester,

[1-(2,2-difluoro-ethyl)-5-(1-isopropyl-piperidin-4-yloxy)-1H-indol-2-yl]-piperazin-1-yl-methanone hydrochloride,

[1-(2,2-difluoro-ethyl)-5-(1-isopropyl-piperidin-4-yloxy)-1H-indol-2-yl]-(4-methanesulfonyl-piperazin-1-yl)-methanone, 1-{4-[1-isopropyl-5-(1-isopropyl-piperidin-4-yloxy)-1H-indole-2-carbonyl]-piperazin-1-yl}-ethanone,

[5-(1-isopropyl-piperidin-4-yloxy)-1H-indol-2-yl]-[4-(2,2,2-trifluoro-ethanesulfonyl)-piperazin-1-yl]-methanone, (4-cyclopropanecarbonyl-piperazin-1-yl)-[5-(1-isopropyl-piperidin-4-yloxy)-1H-indol-2-yl]-methanone, 4-[5-(1-isopropyl-piperidin-4-yloxy)-1H-indole-2-carbonyl]-piperazine-1-carboxylic acid methyl ester, 4-[5-(1-isopropyl-piperidin-4-yloxy)-1H-indole-2-carbonyl]-piperazine-1-carboxylic acid dimethylamide, 4-[5-(1-isopropyl-piperidin-4-yloxy)-1H-indole-2-carbonyl]-piperazine-1-carboxylic acid diethylamide,

[1-(2,2-difluoro-ethyl)-5-(1-isopropyl-piperidin-4-yloxy)-1H-indol-2-yl]-[4-(propane-2-sulfonyl)-piperazin-1-yl]-methanone, (4-cyclopropanecarbonyl-piperazin-1-yl)-[1-(2,2-difluoro-ethyl)-5-(1-isopropyl-piperidin-4-yloxy)-1H-indol-2-yl]-methanone,

[1-(2,2-difluoro-ethyl)-5-(1-isopropyl-piperidin-4-yloxy)-1H-indol-2-yl]-[4-(2,2,2-trifluoro-ethanesulfonyl)-piperazin-1-yl]-methanone, 4-[1-(2,2-difluoro-ethyl)-5-(1-isopropyl-piperidin-4-yloxy)-1H-indol-2-carbonyl]-piperzine-1-carboxylic acid methyl ester, 4-[1-(2,2-difluoro-ethyl)-5-(1-isopropyl-piperidin-4-yloxy)-1H-indole-2-carbonyl]-piperazine-1-carboxylic acid dimethylamide, 4-[1-(2,2-difluoro-ethyl)-5-(1-isopropyl-piperidin-4-yloxy)-1H-indole-2-carbonyl]-piperazine-1-carboxylic acid diethylamide,

[1-(2,2-difluoro-ethyl)-5-(1-isopropyl-piperidin-4-yloxy)-1H-indol-2-yl]-(4-trifluoromethanesulfonyl-piperazin-1-yl)-methanone, 4-[1-(2,2-difluoro-ethyl)-5-(1-isopropyl-piperidin-4-yloxy)-1H-indole-2-carbonyl]-piperazine-1-sulfonic acid dimethylamide,

[1-isopropyl-5-(1-isopropyl-piperidin-4-yloxy)-1H-indol-2-yl]-[4-(propane-2-sulfonyl)-piperazin-1-yl]-methanone, (4-cyclopropanecarbonyl-piperazin-1-yl)-[1-isopropyl-5-(1-isopropyl-piperidin-4-yloxy)-1H-indol-2-yl]-methanone,

[1-isopropyl-5-(1-isopropyl-piperidin-4-yloxy)-1H-indol-2-yl]-[4-(2,2,2-trifluoro-ethanesulfonyl)-piperazin-1-yl]-methanone, 4-[1-isopropyl-5-(1-isopropyl-piperidin-4-yloxy)-1H-indole-2-carbonyl]-piperazine-1-carboxylic acid methyl ester, 4-[1-isopropyl-5-(1-isopropyl-piperidin-4-yloxy)-1H-indole-2-carbonyl]-piperazine-1-carboxylic acid dimethylamide, 4-[1-isopropyl-5-(1-isopropyl-piperidin-4-yloxy)-1H-indole-2-carbonyl]-piperazine-1-carboxylic acid diethylamide,

[1-isopropyl-5-(1-isopropyl-piperidin-4-yloxy)-1H-indol-2-yl]-(4-trifluoromethanesulfonyl-piperazin-1-yl)-methanone, 4-[1-isopropyl-5-(1-isopropyl-piperidin-4-yloxy)-1H-indole-2-carbonyl]-piperazine-1-sulfonic acid dimethylamide, 4-{5-[1-(2,2,2-trifluoro-ethyl)-piperidin-4-yloxy]-1H-indole-2-carbonyl}-piperazine-1-carboxylic acid methyl ester, 4-{1-isopropyl-5-[1-(2,2,2-trifluoro-ethyl)-piperidin-4-yloxy]-1H-indole-2-carbonyl}-piperazine-1-carboxylic acid methyl ester, and pharmaceutically acceptable salts thereof.

Especially preferred are the following compounds:

[6-bromo-5-(1-isopropyl-piperidin-4-yloxy)-1H-indol-2-yl]-(4-methanesulfonyl-piperazin-1-yl)-methanone,

[6-bromo-1-isopropyl-5-(1-isopropyl-piperidin-4-yloxy)-1H-indol-2-yl]-(4-methanesulfonyl-piperazin-1-yl)-methanone,

[6-bromo-5-(1-isopropyl-piperidin-4-yloxy)-1H-indol-2-yl]-(4-ethanesulfonyl-piperazin-1-yl)-methanone,

[6-bromo-1-isopropyl-5-(1-isopropyl-piperidin-4-yloxy)-1H-indol-2-yl]-(4-ethanesulfonyl-piperazin-1-yl)-methanone,

[6-bromo-1-isopropyl-5-(1-isopropyl-piperidin-4-yloxy)-1H-indol-2-yl]-[4-(propane-2-sulfonyl)-piperazin-1-yl]-methanone,

[6-chloro-5-(1-isopropyl-piperidin-4-yloxy)-1H-indol-2-yl]-(4-methanesulfonyl-piperazin-1-yl)-methanone,

[5-(1-isopropyl-piperidin-4-yloxy)-1H-indol-2-yl]-(4-methanesulfonyl-piperazin-1-yl)-methanone,

[1-(2,2-difluoro-ethyl)-5-(1-isopropyl-piperidin-4-yloxy)-1H-indol-2-yl]-(4-methanesulfonyl-piperazin-1-yl)-methanone, (4-cyclopropanecarbonyl-piperazin-1-yl)-[1-(2,2-difluoro-ethyl)-5-(1-isopropyl-piperidin-4-yloxy)-1H-indol-2-yl]-methanone, 4-[1-(2,2-difluoro-ethyl)-5-(1-isopropyl-piperidin-4-yloxy)-1H-indole-2-carbonyl]-piperazine-1-carboxylic acid methyl ester, 4-[1-isopropyl-5-(1-isopropyl-piperidin-4-yloxy)-1H-indole-2-carbonyl]-piperazine-1-carboxylic acid methyl ester, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the formula II

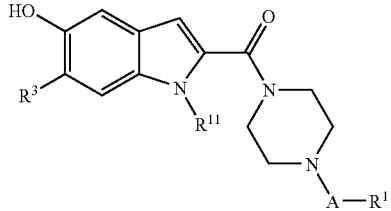

wherein $R^1$ and $R^3$ are as defined herein before and $R^{II}$ is hydrogen or tert-butoxycarbonyl, with an alcohol of the formula III $$HO-R^4 \quad\quad III$$

wherein $R^4$ is as defined herein before, in the presence of a trialkylphosphine or triphenylphosphine and of an azo compound to obtain a compound of the formula IA

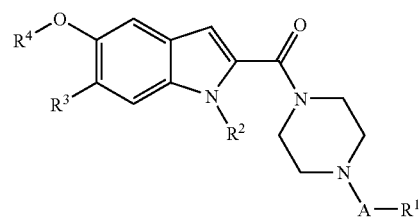

wherein $R^2$ is hydrogen, and optionally transferring into a compound of formula IB

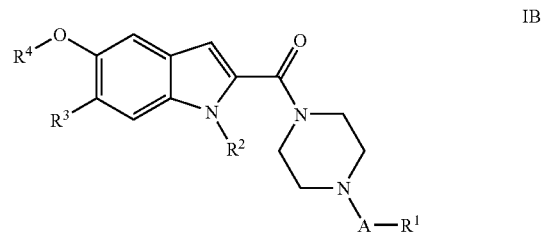

wherein $R^2$ is a group as defined herein before other than hydrogen, and if desired, converting the compound obtained into a pharmaceutically acceptable salt.

An azo compound means for example an azodicarboxylic acid dialkyl ester such as, e.g. diethyl azodicarboxylate (DEAD) or diisopropyl-azodicarboxylate (DIAD) (optionally polymer bound), di-tert-butylazodicarboxylate, or N,N,N',N'-tetramethylazo-dicarboxamide.

In more detail, the compounds of formula I can be manufactured by the methods given below, by the methods given in the examples or by analogous methods. The substituents and indices used in the following description of the processes have the significance given herein before unless indicated to the contrary. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

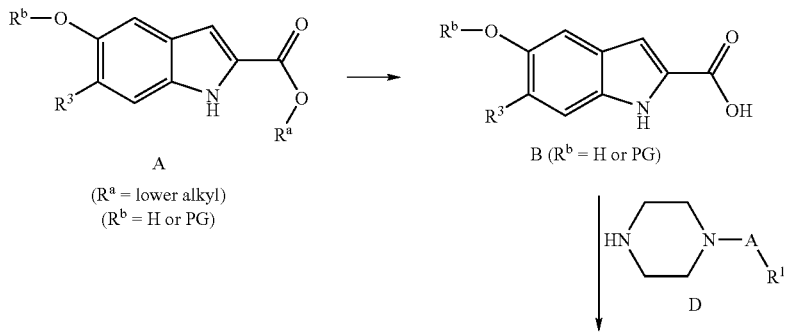

-continued

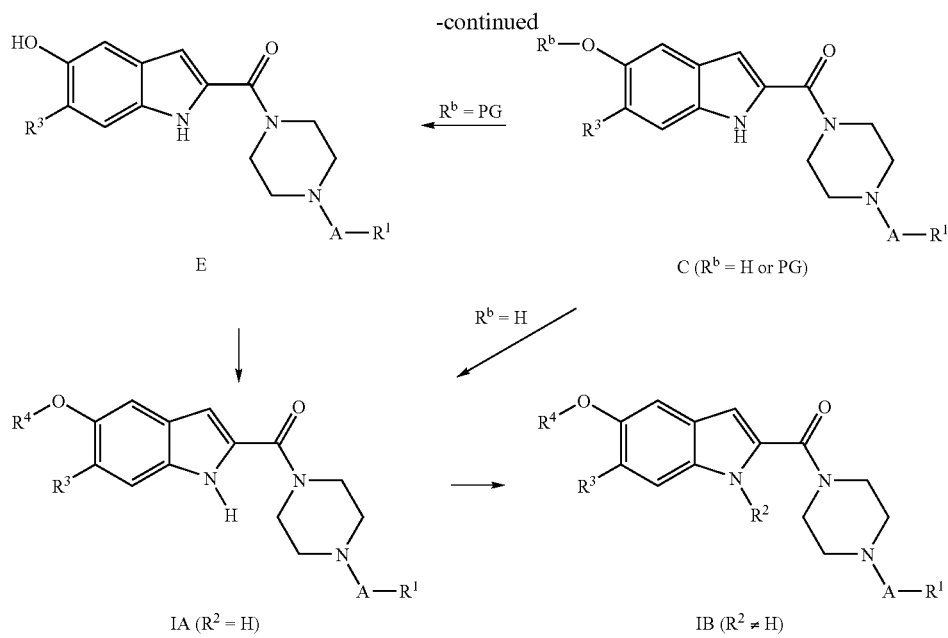

Compounds of the general formula IA and IB can be prepared according to scheme 1. The ester functionality in intermediates A (prepared according to literature procedures, e.g. $R^3$=Br: Chem. Pharm. Bull. 1990, 38, 59; $R^3$=Me: J. Med. Chem. 2001, 44, 3545; $R^3$=Cl: prepared according to Chemical & Pharmaceutical Bulletin 1974, 22(9), 1981-9; WO 2001051466) is cleaved under basic (e.g. with lithium hydroxide in polar solvents such as, e.g. methanol, water or THF or mixtures of said solvents) or under acidic conditions (e.g. using concentrated hydrochloric acid in THF) and subsequent transformation of the resulting lithium or hydrochloride salt of intermediates B to the amide intermediates C by reaction with piperazine derivatives D (either commercially available or accessible by methods described in references, e.g. S. Scapecchi et al., Bioorg. Med. Chem. 2004, 12, 71-85, or by methods known in the art). The coupling of carboxylic acids with amines (either commercially available or accessible by methods described in references or by methods known in the art) is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N-carbonyldiimidazole (CDI), N-(3-Dimethylaminopropyl)-N'-ethyl-carbodiimide hydrochloride (EDCI), 1-hydroxy-1,2,3-benzotriazole (HOBT) or O-benzotriazol-1-yl-N,N,N,N-tetramethyluronium tetrafluoroborate (TBTU) in a suitable solvent such as, e.g. dimethylformamide (DMF) or dioxane in the presence of a base (e.g. triethylamine or diisopropylethylamine). In intermediates C in which the aromatic oxygen is protected by a protective group (PG) compatible with the chemical transformations, the protective group is cleaved of by methods known to those skilled in the art or as described in literature (e.g. as described in T. W. Greene and P. G. M. Wuts, Protective groups in organic synthesis, $3^{rd}$ edition, 1999) to afford intermediates E. For example, a benzyl protective group can be cleaved off by e.g. hydrogenolysis using an appropriate catalyst (e.g. palladium on charcoal) in a suitable solvent or solvent mixture (e.g. ethyl acetate, methanol). A methyl protective group can be cleaved off by, e.g. treatment with boron tribromide in dichloromethane. In case of $R^{4a}$ or $R^{4b}$, the resulting phenol is coupled with alcohols of the type HO—$R^{4a}$ or HO—$R^{4b}$ (either commercially available or accessible by methods described in references or by methods known in the art) applying the so-called "Mitsunobu reaction" which is known to those skilled in the art and widely described (e.g. Hughes, David L. The Mitsunobu reaction. Organic Reactions (New York) 1992, 42, 335-656.). Thereby the phenol intermediate is coupled with alcohols of the type HO—$R^{4a}$ or HO—$R^{4b}$ using a phosphine such as, e.g. tributylphosphine or triphenylphosphine and either an azodicarboxylic acid dialkyl ester such as, e.g. diethyl azodicarboxylate (DEAD) or diisopropyl-azodicarboxylate (DIAD) or using N,N,N',N'-tetramethylazodicarboxamide in a solvent commonly used in such transformations such as, e.g. tetrahydrofuran (THF), toluene or dichloromethane. In cases where the substituents $R^7$ or $R^8$ are not already present in the alcohols of the type HO—$R^{4a}$ or HO—$R^{4b}$, they can be introduced by alkylation of the free amine functionality in compounds of formula IA or IB by employing methods described in references or by methods known in the art such as, e.g. reductive amination (e.g. F. Zaragoza, et. al, J. Med. Chem. 2004, 47, 2833-2838). To this extent, compounds of formula IA might be protected first with a suitable protective group such as, e.g. tert-butoxycarbonyl, which after introduction of $R^7$ or $R^8$ can be removed under conditions known those skilled in the art and as described under scheme 1.

Intermediates of formula IB can be obtained through treatment of intermediates of formula IA with a suitable base in a suitable solvent under anhydrous conditions (e.g. sodium hydride in DMF or cesium carbonate in acetonitrile) and reacting the intermediate anion with an alkylating or acylating agent $R^2$-LG such as, e.g. methyl iodide, 2-bromopropane, 2,2,2-trifluoroethyl-methanesulfonate, 2,2-difluoroethyl-trifluoromethanesulfonate or methanesulfonyl chloride. In those cases $R^2$ signifies a methyl, trifluoromethyl, difluoroethyl, isopropyl or a sulfonyl group and LG signifies a leaving group such as, e.g. iodide, bromide, methanesulfonate, trifluoromethanesulfonate or chloride. Additionally, compounds of formula IB where $R^2$ signifies a phenyl or a substituted phenyl group may be synthesized by processes known to those skilled in the art and described in literature (e.g. W. W. K. R. Mederski et. al, Tetrahedron, 1999, 55, 12757). For example, intermediates of formula IA are reacted with an optionally substituted phenylboronic acid using an appropriate catalyst (e.g. copper(II) acetate) and base (e.g. pyridine) in a suitable solvent such as, e.g. dichloromethane.

$R^a$ in Scheme 1 is an alkyl group, preferably a lower alkyl group, preferably methyl or ethyl.

where $X-R^1$ is a protecting group PG, such as for example tert-butyloxycarbonyl or benzyloxycarbonyl, to afford intermediate L. The protecting group of L may be removed by methods known in the art (for example, when PG is tert-butyloxycarbonyl, it may be removed with an acid, such as for example trifluoroacetic acid, in a suitable solvent, such as for example dichloromethane, or with for example hydrogen chloride, in a suitable solvent, such as ethyl acetate or an alcohol or mixtures thereof) to afford intermediates M, which may be reacted with acid chlorides, sulfonyl chlorides, alkyl chloroformates, or sulfamoyl chlorides with a suitable base in

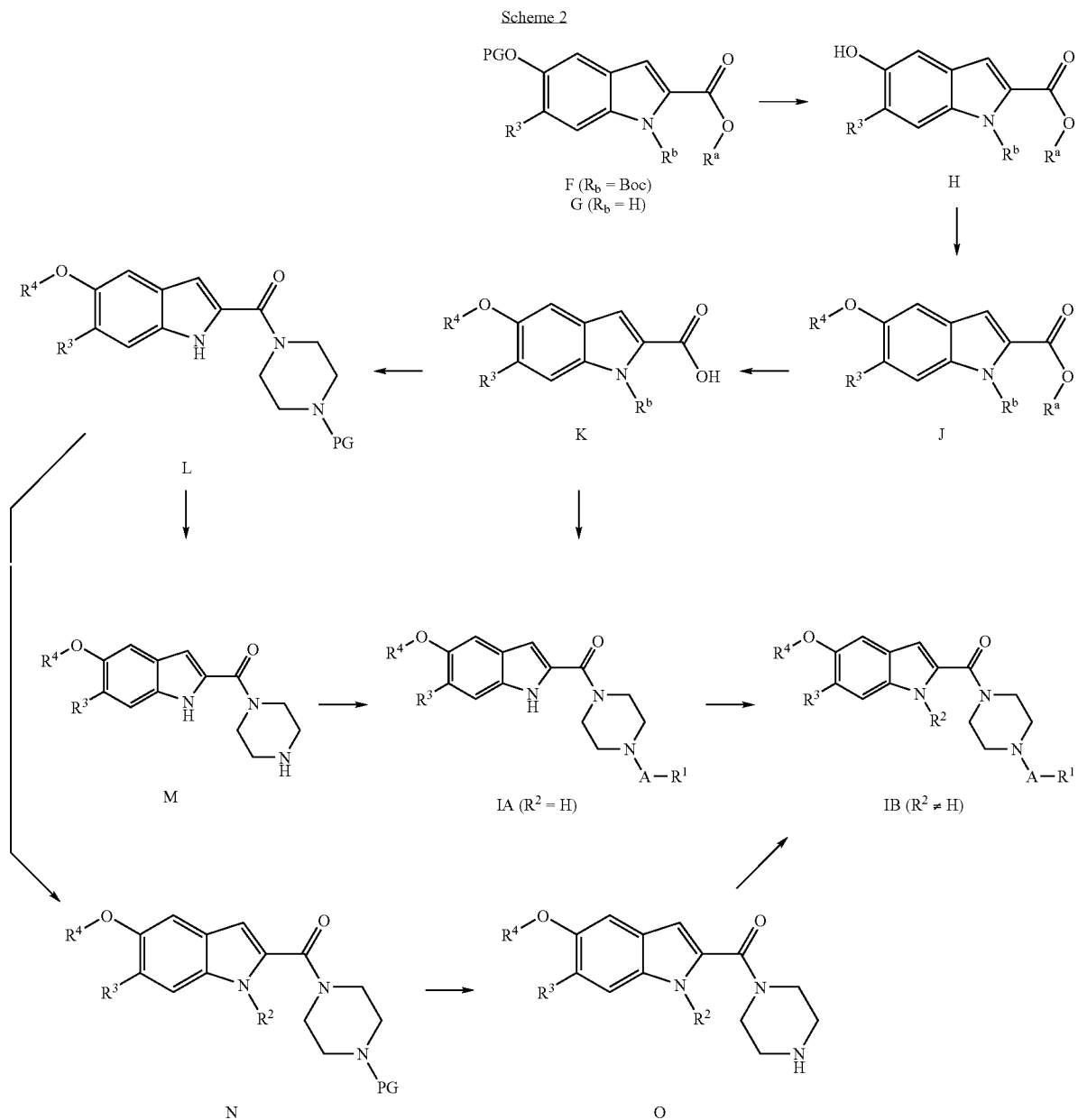

Compounds of the general formula IA and IB can be also prepared according to scheme 2 applying the methods described and mentioned for scheme 1. Alternatively, intermediate K may be reacted with a protected piperazine D, a suitable solvent, according to methods known in the art. Alternatively, intermediates of type N may be prepared from L by treatment with a suitable base in a suitable solvent under anhydrous conditions (e.g. sodium hydride in DMF or cesium carbonate in acetonitrile) and reacting the intermediate anion with an alkylating or acylating agent $R^2$-LG such as, e.g. methyl iodide, 2-bromopropane, 2,2,2-trifluoroethyl-methanesulfonate, 2,2-difluoroethyl-trifluoromethanesulfonate or methanesulfonyl chloride. In those cases $R^2$ signifies a methyl, trifluoromethyl, difluoroethyl, isopropyl or a sulfonyl group and LG signifies a leaving group such as, e.g. iodide, bromide, methanesulfonate, trifluoromethanesulfonate or chloride. The protecting group of intermediates of formula N may be removed by methods known in the art (for example, when PG is tert-butyloxycarbonyl, it may be removed with an acid, such as for example trifluoroacetic acid, in a suitable solvent, such as for example dichloromethane, or with for example hydrogen chloride, in a suitable solvent, such as ethyl acetate or an alcohol or mixtures thereof) to afford intermediates of formula O, which may be reacted with acid chlorides, sulfonyl chlorides, alkyl chloroformates, or sulfamoyl chlorides with a suitable base in a suitable solvent, according to methods known in the art, to provide compounds of formula IB.

For intermediates in which $R^b$ signifies a protective group such as, e.g. a tert-butoxycarbonyl group, the protective group is cleaved after amide formation to give compounds of the general formula IA. $R^a$ in Scheme 2 is an alkyl group, preferably a lower alkyl group, preferably methyl or ethyl. $R^b$ signifies hydrogen or a protective group compatible with the chemical transformations such as, e.g. tert-butoxycarbonyl.

ence of a catalyst such as, e.g. tetrakis(triphenylphosphine) palladium(0) and an appropriate base such as, e.g. sodium carbonate in a solvent mixture such as, e.g. dimethoxyethane and water. The compounds of formula I can contain several asymmetric centres and can be present in the form of optically pure enantiomers, mixtures of enantiomers such as, e.g. racemates, optically pure diastereomers, mixtures of diastereomers, diastereomeric racemates or mixtures of diastereomeric racemates. The optically active forms can be obtained for example by resolution of the racemates, by asymmetric synthesis or asymmetric chromatography (chromatography with a chiral adsorbent or eluant).

As described above, the compounds of formula I of the present invention can be used as pharmaceutical compositions for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addic-

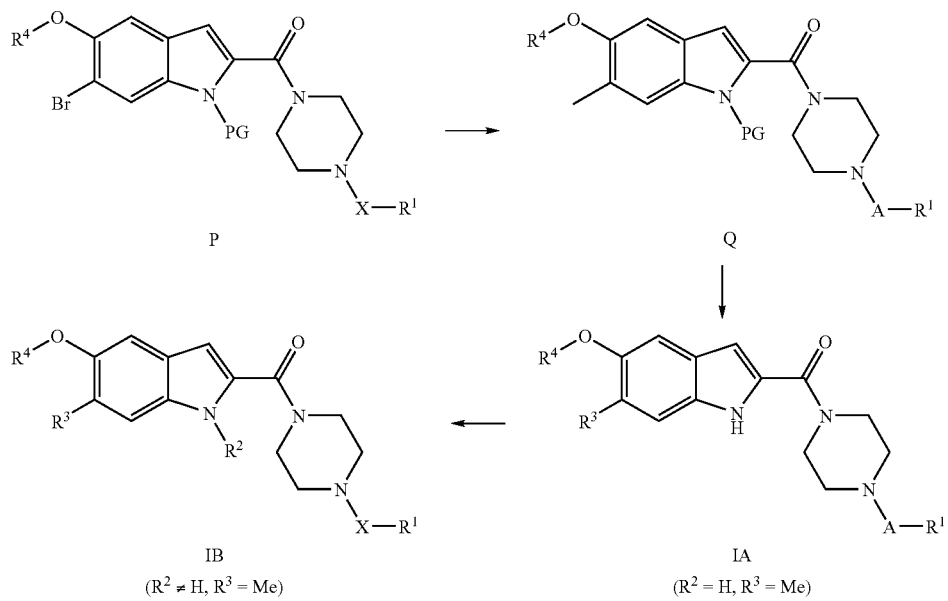

Scheme 3

Another option for preparing compounds of the general formula IA and IB is described in scheme 3. The bromo substituent in intermediates P, obtainable according to the methods described in schemes 1 and 2, can be exchanged for several other substituents such as, e.g. a methyl group, by applying metallo-organic and transition metal-catalyzed reactions known by those skilled in the art and as described in literature (e.g. as described in M. B. Smith and J. March, March's advanced organic chemistry, $5^{th}$ edition, 2001). For example, a methyl group in Q can be introduced through cross-coupling reaction with trimethylboroxine in the prestion, motion sickness and sleep disorders including narcolepsy, and other diseases including asthma, allergy, allergy-induced airway responses, congestion, chronic obstructive pulmonary disease and gastro-intestinal disorders. In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of pharmaceutical compositions for the treatment and prevention of obesity in a patient who is also receiving treatment with a lipase inhibitor and particularly, wherein the lipase inhibitor is orlistat.

It is a further preferred object of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine. Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an object of the present invention.

The use of a compound of formula I in the manufacture of a medicament for the treatment and prevention of obesity in a patient who is also receiving treatment with a lipase inhibitor, preferably with tetrahydrolipstatin, is also an object of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an object of the invention is the method as described above for the simultaneous, separate or sequential administration of a compound according to formula I and a lipase inhibitor, particularly tetrahydrolipstatin. It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent. The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an object of the invention is the method as described above for the simultaneous, separate or sequential administration of a compound according to formula I and a therapeutically effective amount of an anti-diabetic agent.

The use of a compound of formula I in the manufacture of a pharmaceutical compositions for the treatment and prevention of Type II diabetes in a patient who is also receiving treatment with an anti-diabetic agent is also an object of the present invention.

It is a further preferred object to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an object of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an object of the present invention.

It is a further preferred object to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan, A308165, and the like. Also an object of the invention is the method as described above for the simultaneous, separate or sequential administration of a compound according to formula I and a therapeutically effective amount of an anti-hypertensive agent.

The use of a compound of formula I in the manufacture of a medicament for the treatment and prevention of hypertension in a patient who is also receiving treatment with an anti-hypertensive agent, is also an object of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula I.

Binding Assay with $^3$H—(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard topcounter after shaking the plates for two hours at 200 rpm at room temperature.

Binding Buffer: 50 mM Tris-HCl pH 7.4 and 5 mM MgCl$_2$× 6H$_2$O pH 7.4. Washing Buffer: 50 mM Tris-HCl pH 7.4 and 5 mM MgCl$_2$×6H$_2$O and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human H3R—CHO cell line. An appropriate amount of protein, e.g. approximately 500 cpm binding of RAMH at Kd, were incubated for 1 hour at room temperature in 250 µl final volume in 96-well plates in presence of $^3$H(R)α-methylhistamine (1 nM final concentration=Kd). Non-specific binding was determined using a 200 fold excess of cold (R)α-methylhistamine dihydrobromide.

All compounds were tested at a single concentration in duplicate. Compounds that showed an inhibition of [$^3$H]-RAMH by more than 50% were tested again to determine IC$_{50}$ in a serial dilution experiment, meaning concentrations were spanning 10 points starting from 4.6×10$^{-6}$ M to 1.0× 10$^{-9}$ M. The dilution factor was 1/2.15 for the whole series. The concentration at which 50% inhibition of the radioligand $^3$H(R)α-methylhistamine is obtained (the IC$_{50}$) is determined from the linear regression of a plot of the logarithm of the concentration versus percent inhibition measured for the different concentrations. Ki's were calculated from IC$_{50}$ based on Cheng-Prusoff equation (Cheng, Y. Prusoff, W H (1973) Biochem Pharmacol 22, 3099-3108): $K_i=IC_{50}/[1+D/Kd]$ wherein D is the concentration of the radioligand and Kd is the binding constant for the radioligand binding to the receptor under the conditions used in the competition experiment.

The compounds of the present invention exhibit $K_i$ values within the range of about 1 nM to about 1000 nM, preferably of about 1 nM to about 100 nM, and more preferably of about 1 nM to about 30 nM, most preferably of about 1 nM to about 20 nM. The following table shows measured values for some selected compounds of the present invention.

|  | $K_i$ (nM) |
| --- | --- |
| Example 3 | 4.3 |
| Example 5 | 3.4 |
| Example 18 | 2.3 |
| Example 28 | 1.8 |
| Example 44 | 2.4 |
| Example 55 | 6.7 |
| Example 73 | 10.4 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner. MS=mass spectrometry.

EXAMPLES

Example 1

[6-Bromo-5-(1-isopropyl-piperidin-4-yloxy)-1H-indol-2-yl]-[4-(piperidine-1-sulfonyl)-piperazin-1-yl]-methanone To a solution of 0.5 g (1.20 mmol) 6-bromo-5-(1-isopropyl-piperidin-4-yloxy)-1H-indole-2-carboxylic acid hydrochloride in 8 mL N,N-dimethylformamide, 0.48 g (1.50 mmol) O-(benzotriazol-1-yl)-N,N,N',N'-tetramethyluronium tetrafluoroborate, 0.31 g (1.33 mmol) 1-(piperidin-1-yl-sulfonyl)-piperazine and 1.0 mL (0.77 g, 6.0 mmol) N,N-diisopropylethylamine were added. After 2 h the solution was poured on 10% aqueous sodium bicarbonate solution, the phases were separated and the aqueous phase was extracted three times with ethyl acetate. The combined organic layers were washed three times with water followed by brine, dried over magnesium sulfate, filtered and evaporated. The residue was purified by flash chromatography twice on silica gel using a gradient of dichloromethane: methanol (100:0 to 50:50 v/v) as eluant, to afford 0.4 g (56%) of the title compound as a light-yellow foam.

MS (ISP): 596.2 (M+H$^+$)

Intermediates a) 6-Bromo-5-(1-isoopropyl-piperidin-4-yloxy)-1H-indole-2-carboxylic acid; hydrochloride To a solution of 9.8 g (23.9 mmol) 6-bromo-5-(1-isopropyl-piperidin-4-yloxy)-1H-indole-2-carboxylic acid ethyl ester in 400 mL tetrahydrofurane, 0.72 g (30.1 mmol) lithium hydroxide and 200 mL water were added. The solution was stirred for 2 h at reflux temperature and then the organic solvent was removed at a rotary evaporator. The pH was adjusted to 2 using 4M hydrochloric acid and the mixture was evaporated to dryness. The solid was taken up in toluene, evaporated and dried under high vacuum to afford 11.3 g (>100%) of the title compound as a light-yellow solid.

MS (ISP): 381.1 (M+H$^+$)

b) 6-Bromo-5-(1-isopropyl-piperidin-4-yloxy)-1H-indole-2-carboxylic acid ethyl ester To a suspension of 5.7 g (20.0 mmol) 6-bromo-5-hydroxy-1H-indole-2-carboxylic acid ethyl ester in 120 mL tetrahydrofuran, 3.44 g (24.0 mmol) isopropyl-piperidin-4-ol and 6.30 g (24.0 mmol) triphenylphosphine were added. The suspension was cooled to 0° C. and 5.53 g (24.0 mmol) di-tert-butyl azodicarboxylate was added. The ice bath was removed and the reaction mixture was stirred for 18 h at room temperature. The volatile components were removed and the residue was chromatographed on silica gel with dichloromethane:methanol:ammonia (9:1:0.1 v/v) as eluant to afford 6.2 g (76%) of the compound as a light-yellow foam.

c) 6-Bromo-5-hydroxy-1H-indole-2-carboxylic acid ethyl ester

A solution of 8.30 g (27.8 mmol) 6-bromo-5-methoxy-1H-indole-2-carboxylic acid ethyl ester (prepared according to J. Org. Chem. 1974, 39, 3580) in 160 mL dichloromethane was cooled to −78° C. At this temperature, 55.7 mL boron tribromide (55.7 mmol; 1M solution in dichloromethane) were added. The solution was allowed to warm to room temperature and after 30 min. the solution was poured into 10% aqueous sodium bicarbonate solution; the phases were separated and the aqueous phase was extracted three times with ethyl acetate. The combined organic layers were washed with water, brine, dried over magnesium sulfate, filtered and evaporated. The residue was purified by flash chromatography on silica gel with n-hexane:ethyl acetate (2:1 v/v) as eluant to afford 5.7 g (72%) of the product as a light-yellow solid.

MS (ISP): 282.2 (M−H$^+$)

Example 2

[6-Bromo-5-(1-isopropyl-piperidin-4-yloxy)-1H-indol-2-yl]-(4-methanesulfonyl-piperazin-1-yl)-methanone The title compound was synthesized in analogy to example 1, from 6-bromo-5-(1-isopropyl-piperidin-4-yloxy)-1H-indole-2-carboxylic acid hydrochloride (example 1, intermediate a) and 1-methylsulfonyl-piperazine to afford the title compound as a light-yellow solid (45%).

MS (ISP): 527.0 (M+H$^+$)

Example 3

4-[6-Bromo-5-(1-isopropyl-piperidin-4-yloxy)-1H-indole-2-carbonyl]-piperazine-1-sulfonic acid dimethylamide The title compound was synthesized in analogy to example 1, from 6-bromo-5-(1-isopropyl-piperidin-4-yloxy)-1H-indole-2-carboxylic acid; hydrochloride (example 1, intermediate a) and piperazine-1-sulfonic acid dimethylamide to afford the title compound as a light-yellow solid (45%).

MS (ISP): 556.1(M+H$^+$).

Example 4

[6-Bromo-1-isopropyl-5-(1-isopropyl-piperidin-4-yloxy)-1H-indol-2-yl]-[4-(piperidine-1-sulfonyl)-piperazin-1-yl]-methanone To a solution of 100 mg (0.17 mmol) [6-bromo-5-(1-isopropyl-piperidin-4-yloxy)-1H-indol-2-yl]-[4-(piperidine-1-sulfonyl)-piperazin-1-yl]-methanone (example 1) in 3 mL acetonitrile were added 109 mg (0.33 mmol) cesium carbonate and 46 mg (0.33 mmol) isopropyl methanesulfonate. The reaction was stirred under reflux for 18 h. After cooling to room temperature, the reaction mixture was poured into 10% aqueous sodium bicarbonate solution; the phases were separated and the aqueous phase was extracted three times with ethyl acetate. The combined organic layers were washed with brine, dried over magnesium sulfate, filtered and evaporated. The residue was purified by flash chromatography on silica gel with a gradient of dichloromethane:methanol (100:0 to 50:50) as eluant, to afford 60 mg (56%) of the product as a light-yellow oil.

MS (ISP): 638.3 (M+H$^+$)

Example 5

[6-Bromo-1-isopropyl-5-(1-isopropyl-piperidin-4-yloxy)-1H-indol-2-yl]-(4-methanesulfonyl-piperazin-1-yl)-methanone The title compound was synthesized in analogy to example 4, from [6-bromo-5-(1-isopropyl-piperidin-4-yloxy)-1H-indol-2-yl]-(4-methanesulfonyl-piperazin-1-yl)-methanone (example 2) to afford the title compound as a light-yellow solid (51%).

MS (ISP): 569.2 (M+H$^+$).

Example 6

4-[6-Bromo-1-isopropyl-5-(1-isopropyl-piperidin-4-yloxy)-1H-indole-2-carbonyl]-piperazine-1-sulfonic acid dimethylamide The title compound was synthesized in analogy to example 4, from 4-[6-bromo-5-(1-isopropyl-piperidin-4-yloxy)-1H-indole-2-carbonyl]-piperazine-1-sulfonic acid dimethylamide (example 3) to afford to afford the title compound as a light-yellow oil (43%).

MS (ISP): 598.2 (M+H$^+$).

Example 7

[6-Bromo-1-(2-chloro-pyridin-4-yl)-5-(1-isopropyl-piperidin-4-yloxy)-1H-indol-2-yl]-[4-(piperidine-1-sulfonyl)-piperazin-1-yl]-methanone A suspension of 0.15 g (0.25 mmol) [6-bromo-5-(1-isopropyl-piperidin-4-yloxy)-1H-indol-2-yl]-[4-(piperidine-1-sulfonyl)-piperazin-1-yl]-methanone (example 1), 119 mg (0.76 mmol) 2-chloropyridine-4-boronic acid, 91 mg (0.50 mmol) copper(II) acetate and 80 μL (78 mg, 1.0 mmol) pyridine in 4 ml chloroform was stirred 18 h at 35° C. The volatile components were evaporated under reduced pressure and the residue was purified by flash chromatography on silica gel with a gradient of dichloromethane:methanol (100:0 to 50:50 v/v) as eluant to afford 84 mg (47%) of the title compound as a light-yellow solid.

MS (ISP): 707.3 (M+H$^+$).

Example 8

[6-Bromo-1-(2-chloro-pyridin-4-yl)-5-(1-isopropyl-piperidin-4-yloxy)-1H-indol-2-yl]-(4-methanesulfonyl-piperazin-1-yl)-methanone The title compound was synthesized in analogy to example 7, from [6-bromo-5-(1-isopropyl-piperidin-4-yloxy)-1H-indol-2-yl]-(4-methanesulfonyl-piperazin-1-yl)-methanone (example 2) to afford the title compound as a light-yellow solid (27%).

MS (ISP): 638.1 (M+H$^+$).

Example 9

4-[6-Bromo-1-(2-chloro-pyridin-4-yl)-5-(1-isopropyl-piperidin-4-yloxy)-1H-indole-2-carbonyl]-piperazine-1-sulfonic acid dimethylamide The title compound was synthesized in analogy to example 7, from 4-[6-bromo-5-(1-isopropyl-piperidin-4-yloxy)-1H-indole-2-carbonyl]-piperazine-1-sulfonic acid dimethylamide (example 3) to afford the title compound as a light-yellow solid (47%).

MS (ISP): 667.3 (M+H$^+$).

Example 10

[6-Bromo-5-(1-isopropyl-piperidin-4-yloxy)-1H-indol-2-yl]-(4-ethanesulfonyl-piperazin-1-yl)-methanone The title compound was synthesized in analogy to example 1, from 6-bromo-5-(1-isopropyl-piperidin-4-yloxy)-1H-indole-2-carboxylic acid; hydrochloride (example 1, intermediate a) and 1-(ethylsulfonyl)-piperazine to afford the title compound as a light-yellow solid (46%).

MS (ISP): 555.2 (M+H$^+$).

Example 11

[6-Bromo-1-isopropyl-5-(1-isopropyl-piperidin-4-yloxy)-1H-indol-2-yl]-(4-ethanesulfonyl-piperazin-1-yl)-methanone The title compound was synthesized in analogy to example 4, from [6-bromo-5-(1-isopropyl-piperidin-4-yloxy)-1H-indol-2-yl]-(4-ethanesulfonyl-piperazin-1-yl)-methanone (example 10) to afford the title compound as a light-yellow foam (49%).

MS (ISP): 583.3 (M+H$^+$).

Example 12

[6-Bromo-5-(1-isopropyl-piperidin-4-yloxy)-1-(2,2,2-trifluoro-ethyl)-1H-indol-2-yl]-(4-ethanesulfonyl-piperazin-1-yl)-methanone To a solution of 144 mg (0.26 mmol) [6-bromo-5-(1-isopropyl-piperidin-4-yloxy)-1H-indol-2-yl]-(4-ethanesulfonyl-piperazin-1-yl)-methanone (example 10) in 3 mL N,N-dimethylformamide, were added 13 mg (0.29 mmol; 55% dispersion in mineral oil) sodium hydride. The reaction mixture was stirred 15 min at 70° C. 68 mg (0.29 mmol) 2,2,2-Trifluoroethyl methanesulfonate were added and the solution was stirred another 2 h at 70° C. After cooling to room temperature, the reaction was poured into water and the phases were separated. The aqueous phase was extracted three times with ethyl acetate. The combined organic layers were washed with water and brine, dried over magnesium sulfate, filtered and evaporated. The crude product was purified by flash chromatography on silica gel with dichloromethane:methanol:ammonia (9:1:0.1 v/v) as eluant, to afford 86 mg (52%) of the title compound as a light-yellow oil.

MS (ISP): 623.3 (M+H$^+$).

Example 13

[6-Bromo-5-(1-isopropyl-piperidin-4-yloxy)-1H-indol-2-yl]-[4-(propane-2-sulfonyl)-piperazin-1-yl]-methanone The title compound was synthesized in analogy to example 1, from 6-bromo-5-(1-isopropyl-piperidin-4-yloxy)-1H-indole-2-carboxylic acid; hydrochloride (example 1, intermediate a) and 1-(1-methylethylsulfonyl)piperazine (prepared in analogy to International Patent Application Publ. No. WO 2003/064413 using isopropylsulfonyl chloride and tert-butyl 1-piperazinecarboxylate) to afford the title compound as a yellow solid (40%).

MS (ISP): 555.2 (M+H$^+$)

Example 14

[6-Bromo-5-(1-isopropyl-piperidin-4-yloxy)-1H-indol-2-yl]-(4-trifluoromethanesulfonyl-piperazin-1-yl)-methanone The title compound was synthesized in analogy to example 1, from 6-bromo-5-(1-isopropyl-piperidin-4-yloxy)-1H-indole-2-carboxylic acid; hydrochloride (example 1, intermediate a) and 1-trifluoromethanesulfonyl-piperazine (prepared in analogy to International Patent Application Publ. No. WO 2003/064413 by using trifluoromethanesulfonyl chloride and tert-butyl 1-piperazinecarboxylate) to afford the title compound as a yellow solid (48%).

MS (ISP): 581.1 (M+H$^+$)

Example 15

[6-Bromo-1-isopropyl-5-(1-isopropyl-piperidin-4-yloxy)-1H-indol-2-yl]-[4-(propane-2-sulfonyl)-piperazin-1-yl]-methanone The title compound was synthesized in analogy to example 4, from [6-bromo-5-(1-isopropyl-piperidin-4-yloxy)-1H-indol-2-yl]-[4-(propane-2-sulfonyl)-piperazin-1-yl]-methanone (example 13) to afford the title compound as a white solid (34%).

MS (ISP): 597.3 (M+H$^+$)

Example 16

[6-Bromo-1-isopropyl-5-(1-isopropyl-piperidin-4-yloxy)-1H-indol-2-yl]-(4-trifluoromethanesulfonyl-piperazin-1-yl)-methanone The title compound was synthesized in analogy to example 4, from [6-bromo-5-(1-isopropyl-piperidin-4-yloxy)-1H-indol-2-yl]-(4-trifluoromethanesulfonyl-piperazin-1-yl)-methanone (example 14) to afford the title compound as a white solid (44%).

MS (ISP): 623.2 (M+H$^+$).

Example 17

[6-Bromo-5-(1-isopropyl-piperidin-4-yloxy)-1H-indol-2-yl]-(4-cyclopropanesulfonyl-piperazin-1-yl)-methanone The title compound was synthesized in analogy to example 1, from 6-bromo-5-(1-isopropyl-piperidin-4-yloxy)-1H-indole-2-carboxylic acid hydrochloride (example 1, intermediate a) and cyclopropylsulfonyl-piperazine (prepared in analogy to International Patent Application Publ. No. WO 2003/064413 by using cyclopropylsulfonyl chloride and tert-butyl 1-piperazinecarboxylate) to afford the title compound as a light-yellow solid (62%).

MS (ISP): 553.0 (M+H$^+$).

Example 18

[6-Bromo-5-(1-isopropyl-piperidin-4-yloxy)-1H-indol-2-yl]-(4-cyclopropanecarbonyl-piperazin-1-yl)-methanone The title compound was synthesized in analogy to example 1, from 6-bromo-5-(1-isopropyl-piperidin-4-yloxy)-1H-indole-2-carboxylic acid hydrochloride (example 1, intermediate a) and 1-(cyclopropanecarbonyl)piperazine to afford the title compound as a light-yellow foam (48%).

MS (ISP): 517.2 (M+H$^+$).

Example 19

1-{4-[6-Bromo-5-(1-isopropyl-piperidin-4-yloxy)-1H-indole-2-carbonyl]-piperazin-1-yl}-ethanone The title compound was synthesized in analogy to example 1, from 6-bromo-5-(1-isopropyl-piperidin-4-yloxy)-1H-indole-2-carboxylic acid hydrochloride (example 1, intermediate a) and 1-acetylpiperazine to afford the title compound as a light-yellow foam (52%).

MS (ISP): 491.1 (M+H$^+$).

Example 20

[6-Bromo-1-(2-chloro-pyridin-4-yl)-5-(1-isopropyl-piperidin-4-yloxy)-1H-indol-2-yl]-(4-cyclopropanesulfonyl-piperazin-1-yl)-methanone The title compound was synthesized in analogy to example 7, from [6-bromo-5-(1-isopropyl-piperidin-4-yloxy)-1H-indol-2-yl]-(4-cyclopropanesulfonyl-piperazin-1-yl)-methanone (example 17) to afford the title compound as a light-yellow foam (23%).

MS (ISP): 664.1 (M+H$^+$).

Example 21

[6-Bromo-1-(2-chloro-pyridin-4-yl)-5-(1-isopropyl-piperidin-4-yloxy)-1H-indol-2-yl]-(4-cydlopropanecarbonyl-piperazin-1-yl)-methanone The title compound was synthesized in analogy to example 7, from [6-bromo-5-(1-isopropyl-piperidin-4-yloxy)-1H-indol-2-yl]-(4-cyclopropanecarbonyl-piperazin-1-yl)-methanone (example 18) to afford the title compound as a light-yellow foam (35%).

MS (ISP): 628.3 (M+H$^+$).

Example 22

[6-Bromo-1-isopropyl-5-(1-isopropyl-piperidin-4-yloxy)-1H-indol-2-yl]-(4-cyclopropanesulfonyl-piperazin-1-yl)-methanone The title compound was synthesized in analogy to example 4, from [6-bromo-5-(1-isopropyl-piperidin-4-yloxy)-1H-indol-2-yl]-(4-cyclopropanesulfonyl-piperazin-1-yl)-methanone (example 17) to afford the title compound as a light-yellow foam (61%).

MS (ISP): 595.3(M+H$^+$).

Example 23

[6-Bromo-1-isopropyl-5-(1-isopropyl-piperidin-4-yloxy)-1H-indol-2-yl]-(4-cyclopropanecarbonyl-piperazin-1-yl)-methanone The title compound was synthesized in analogy to example 4, from [6-bromo-5-(1-isopropyl-piperidin-4-yloxy)-1H-indol-2-yl]-(4-cyclopropanecarbonyl-piperazin-1-yl)-methanone (example 18) to afford the title compound as a light-yellow foam (50%).

MS (ISP): 559.4 (M+H$^+$).

Example 24

[6-Bromo-1-(2-hydroxy-ethyl)-5-(1-isopropyl-piperidin-4-yloxy)-1H-indol-2-yl]-(4-cyclopropanesulfonyl-piperazin-1-yl)-methanone A solution of 85 mg (0.12 mmol) [6-bromo-1-[2-(tert-butyl-dimethyl-silanyloxy)-ethyl]-5-(1-isopropyl-piperidin-4-yloxy)-1H-indol-2-yl]-(4-cyclopropanesulfonyl-piperazin-1-yl)-methanone in 2 mL dichloromethane was cooled to 0° C. and 1.0 mL (1.49 g, 13.1 mmol) trifluoroacetic acid were added. The cooling bath was removed and after stirring for 1 h at room temperature the solution was evaporated to dryness. The residue was taken up in dichloromethane and extracted with 1M aqueous sodium hydroxide solution. The organic layer was washed with brine, dried over magnesium sulfate, filtered and evaporated to afford 71 mg (99%) of the title compound as colourless oil.

MS (ISP): 597.2 (M+H$^+$).

Intermediate

[6-Bromo-1-[2-(tert-butyl-dimethyl-silanyloxy)-ethyl]-5-(1-isopropyl-piperidin-4-yloxy)-1H-indol-2-yl]-(4-cyclopropanesulfonyl-piperazin-1-yl)-methanone The title compound was prepared in analogy to example 12, from [6-bromo-5-(1-isopropyl-piperidin-4-yloxy)-1H-indol-2-yl]-(4-cyclopropanesulfonyl-piperazin-1-yl)-methanone (example 17), sodium hydride and (2-bromoethoxy)-tert-butyldimethylsilane in N,N-dimethylformamide, to afford the title compound as a colourless foam (36%).

MS (ISP): 711.2 (M+H$^+$).

Example 25

[6-Bromo-1-(2-hydroxy-ethyl)-5-(1-isopropyl-piperidin-4-yloxy)-1H-indol-2-yl]-(4-cyclopropanecarbonyl-piperazin-1-yl)-methanone The title compound was synthesized in analogy to example 24, from [6-bromo-1-[2-(tert-butyl-dimethyl-silanyloxy)-ethyl]-5-(1-isopropyl-piperidin-4-yloxy)-1H-indol-2-yl]-(4-cyclopropanecarbonyl-piperazin-1-yl)-methanone to afford the title compound as a white foam (99%).

MS (ISP): 561.4 (M+H$^+$).

Intermediate

[6-Bromo-1-[2-(tert-butyl-dimethyl-silanyloxy)-ethyl]-5-(1-isopropyl-piperidin-4-yloxy)-1H-indol-2-yl]-(4-cyclopropanecarbonyl-piperazin-1-yl)-methanone The title compound was synthesized in analogy to example 24 (intermediate), from [6-bromo-5-(1-isopropyl-piperidin-4-yloxy)-1H-indol-2-yl]-(4-cyclopropanecarbonyl-piperazin-1-yl)-methanone (example 18) to afford the title compound as colourless foam (64%).

MS (ISP): 675.3 (M+H$^+$).

Example 26

1-{4-[6-Bromo-1-(2-hydroxy-ethyl)-5-(1-isopropyl-piperidin-4-yloxy)-1H-indole-2-carbonyl]-piperazin-1-yl}-ethanone The title compound was synthesized in analogy to example 24, from 1-{4-[6-bromo-1-[2-(tert-butyl-dimethyl-silanyloxy)-ethyl]-5-(1-isopropyl-piperidin-4-yloxy)-1H-indole-2-carbonyl]-piperazin-1-yl}-ethanone to afford the title compound as a colourless oil (99%).

MS (ISP): 5.35.3 (M+H$^+$)

Intermediate

1-{4-[6-Bromo-1-[2-(tert-butyl-dimethyl-silanyloxy)-ethyl]-5-(1-isopropyl-piperidin-4-yloxy)-1H-indole-2-carbonyl]-piperazin-1-yl}-ethanone The title compound was synthesized in analogy to example 24 (intermediate), from 1-{4-[6-bromo-5-(1-isopropyl-piperidin-4-yloxy)-1H-indole-2-carbonyl]-piperazin-1-yl}-ethanone (example 19) to afford the title compound as white foam (55%).

MS (ISP): 649.4 (M+H$^+$).

Example 27

1-{4-[6-Bromo-1-isopropyl-5-(1-isopropyl-piperidin-4-yloxy)-1H-indole-2-carbonyl]-piperazin-1-yl}-ethanone The title compound was synthesized in analogy to example 4, from 1-{4-[6-bromo-5-(1-isopropyl-piperidin-4-yloxy)-1H-indole-2-carbonyl]-piperazin-1-yl}-ethanone (example 19) to afford the title compound as light-yellow oil (60%).

MS (ISP): 533.3 (M+H$^+$).

Example 28

1-{4-[6-Bromo-1-(2-chloro-pyridin-4-yl)-5-(1-isopropyl-piperidin-4-yloxy)-1H-indole-2-carbonyl]-piperazin-1-yl}-ethanone The title compound was synthesized in analogy to example 7, from 1-{4-[6-bromo-5-(1-isopropyl-piperidin-4-yloxy)-1H-indole-2-carbonyl]-piperazin-1-yl}-ethanone (example 19) to afford the title compound as a light-yellow solid (33%).

MS (ISP): 602.2 (M+H$^+$).

Example 29

[5-(1-Isopropyl-piperidin-4-yloxy)-6-methyl-1H-indol-2-yl]-(4-methanesulfonyl-piperazin-1-yl)-methanone The title compound was synthesized in analogy to example 1, from 5-(1-isopropyl-piperidin-4-yloxy)-6-methyl-1H-indole-2-carboxylic acid hydrochloride and 1-methanesulfonylpiperazine to afford the title compound as a light-yellow solid (49%).

MS (ISP): 463.1 (M+H$^+$).

Intermediates a) 5-(1-Isopropyl-piperidin-4-yloxy)-6-methyl-1H-indole-2-carboxylic acid; hydrochloride To a solution of 1.4 g (0.41 mmol) 5-(1-isopropyl-piperidin-4-yloxy)-6-methyl-1H-indole-2-carboxylic acid ethyl ester in 70 mL tetrahydrofuran was added a solution of 0.122 g (0.51 mmol) lithium hydroxide dissolved in 35 mL water. The reaction was heated under reflux for 18 hours. The organic solvent was removed under reduced pressure and the pH of the remaining aqueous solution was adjusted to 2 using 4M hydrochloric acid. After evaporation to dryness, the residue was taken up in toluene, the suspension was reevaporated and dried under high vacuum to afford the title compound as a light brown solid (>100%) which was pure enough to be used in the next step without further purification.

MS (ISP): 317.0 (M+H$^+$).

b) 5-(1-Isopropyl-piperidin-4-yloxy)-6-methyl-1H-indole-2-carboxylic acid ethyl ester To a suspension of 0.125 g (0.57 mmol) 5-hydroxy-6-methyl-1H-indole-2-carboxylic acid ethyl ester in 3 mL tetrahydrofuran, 98 mg (0.68 mmol) 1-isopropyl-piperidin-4-ol and 0.18 g (0.68 mmol) triphenylphosphine were added. The reaction was cooled to 0° C., 0.16 g (0.68 mmol) di-tert-butyl azodicarboxylate were added and the cooling bath was removed. After stirring 18 h at room temperature the volatile components were evaporated and the residue was purified by flash chromatography on silica gel using a gradient of dichloromethane:methanol (100:0 to 50:50 v/v) as eluant, to afford 74 mg (38%) of the title compound as a light-yellow foam.

MS (EI): 345.2 (M).

c) 5-Hydroxy-6-methyl-1H-indole-2-carboxylic acid ethyl ester

A solution of 0.13 g (0.56 mmol) 5-methoxy-6-methyl-1H-indole-2-carboxylic acid ethyl ester in 3 mL dichloromethane was cooled to −78° C. 1.11 mL (1.1 mmol, 1 M solution in dichloromethane) boron tribromide were added and the cooling bath was removed. After stirring 2 h at room temperature, the solution was poured into 10% aqueous sodium bicarbonate solution and the phases were separated. The aqueous layer was extracted three times with ethyl acetate and the combined organic layers were washed with brine, dried over magnesium sulfate, filtered and evaporated. The residue was purified by flash chromatography on silica gel using a gradient of n-heptane: ethyl acetate (100:0 to 70:30 v/v) as eluant, to afford 53 mg (43%) of the title compound as a light-yellow solid.

MS (EI): 219.1 (M).

d) 5-Methoxy-6-methyl-1H-indole-2-carboxylic acid ethyl ester

A solution of 0.20 g (0.60 mmol) 5-methoxy-6-methyl-indole-1,2-dicarboxylic acid 1-tert-butyl ester 2-ethyl ester in 4 mL dichloromethane was cooled to 0° C. and 2 mL (3.0 g, 26.1 mmol) trifluoroacetic acid were added. The ice bath was removed and after stirring 1 h at room temperature the solution was evaporated to dryness. The residue was dissolved in dichloromethane, washed with aqueous 1M sodium hydroxide solution and brine, dried over magnesium sulfate, filtered and evaporated to afford the title compound as a white solid (97%) which was pure enough to be used in the next step.

MS (EI): 233.2 (M).

e) 5-Methoxy-6-methyl-indole-1,2-dicarboxylic acid 1-tert-butyl ester 2-ethyl ester To a solution of 0.20 g (0.50 mmol) 6-bromo-5-methoxy-indole-1,2-dicarboxylic acid 1-tert-butyl ester 2-ethyl ester in 8 mL 1,2-dimethoxyethane were added 58 µg (0.050 mmol) tetrakis(triphenylphosphine)palladium(0). After stirring 30 min at room temperature, 76 µg (0.60 mmol) trimethylboroxine and 0.16 g (1.50 mmol) sodium carbonate dissolved in 4 mL water were added and the reaction mixture was heated 3 h at reflux. The solution was poured into 10% aqueous sodium bicarbonate solution and ethyl acetate, the layers were separated and the aqueous layer was extracted three times with ethyl acetate. The combined organic layers were washed with brine, dried over magnesium sulfate, filtered and evaporated. The residue was purified twice by flash chromatography on silica gel using a gradient of dichloromethane:methanol (100:0 to 50:50 v/v) as eluant, to afford 95 mg (57%) of the title compound as colourless oil.

MS (ISP): 334.2 (M+H$^+$).

f) 6-Bromo-5-methoxy-indole-1,2-dicarboxylic acid 1-tert-butyl ester 2-ethyl ester A solution of 20.0 g (67.1 mmol) 6-bromo-5-methoxy-1H-indole-2-carboxylic acid ethyl ester (prepared according to Chem. Pharm. Bull. 1990, 38, 59-64), 17.6 g (80.5 mmol) di-tert-butyl dicarbonate and 0.82 g (6.71 mmol) 4-dimethylaminopyridine in 200 mL dichloromethane was stirred at room temperature for 1 h. The volatile components were evaporated under reduced pressure and the residue was purified by flash chromatography on silica gel with n-hexane: ethyl acetate (4:1 v/v) as eluant to afford 26.9 g (100%) of the compound as a light-yellow oil.

MS (ISP): 397.9 (M+H$^+$).

Example 30

4-[5-(1-Isopropyl-piperidin-4-yloxy)-6-methyl-1H-indole-2-carbonyl]-piperazine-1-carboxylic acid ethyl ester The title compound was synthesized in analogy to example 1, from 5-(1-isopropyl-piperidin-4-yloxy)-6-methyl-1H-indole-2-carboxylic acid hydrochloride and 1-ethoxycarbonylpiperazine to afford the title compound as a light-yellow foam (65%).

MS (ISP): 457.3 (M+H$^+$).

Example 31

(4-Cyclopropanecarbonyl-piperazin-1-yl)-[5-(1-isopropyl-piperidin-4-yloxy)-6-methyl-1H-indol-2-yl]-methanone The title compound was synthesized in analogy to example 1, from 5-(1-isopropyl-piperidin-4-yloxy)-6-methyl-1H-indole-2-carboxylic acid hydrochloride and 1-(cyclopropanecarbonyl)piperazine to afford the title compound as a light-yellow foam (56%).

MS (ISP): 453.3 (M+H$^+$).

Example 32

[1-Isopropyl-5-(1-isopropyl-piperidin-4-yloxy)-6-methyl-1H-indol-2-yl]-(4-methanesulfonyl-piperazin-1-yl)-methanone The title compound was synthesized in analogy to example 4, from [5-(1-isopropyl-piperidin-4-yloxy)-6-methyl-1H-indol-2-yl]-(4-methanesulfonyl-piperazin-1-yl)-methanone (example 29), cesium carbonate and isopropyl methanesulfonate, to afford the title compound as a light-yellow oil (9%).

MS (ISP): 505.2 (M+H$^+$).

Example 33

(4-Cyclopropanecarbonyl-piperazin-1-yl)-[1-isopropyl-5-(1-isopropyl-piperidin-4-yloxy)-6-methyl-1H-indol-2-yl]-methanone The title compound was synthesized in analogy to example 4, from (4-cyclopropanecarbonyl-piperazin-1-yl)-[5-(1-isopropyl-piperidin-4-yloxy)-6-methyl-1H-indol-2-yl]-methanone (example 33) to afford the title compound as a light-yellow solid (21%).

MS (ISP): 495.3 (M+H$^+$).

Example 34

4-[1-Isopropyl-5-(1-isopropyl-piperidin-4-yloxy)-6-methyl-1H-indole-2-carbonyl]-piperazine-1-carboxylic acid ethyl ester The title compound was synthesized in analogy to example 4, from 4-[5-(1-isopropyl-piperidin-4-yloxy)-6-methyl-1H- indole-2-carbonyl]-piperazine-1-carboxylic acid ethyl ester (example 32) to afford the title compound as a light-yellow solid (8%).

MS (ISP): 499.2 (M+H$^+$).

Example 35

4-[6-Chloro-5-(1-isopropyl-piperidin-4-yloxy)-1H-indole-2-carbonyl]-piperazine-1-carboxylic acid tert-butyl ester A mixture of 6-chloro-5-(1-isopropyl-piperidin-4-yloxy)-1H-indole-2-carboxylic acid hydrochloride salt with 1 eq. lithium chloride (760 mg, 1.0 eq.), tert-butyl-1-piperazinecarboxylate (467 mg, 1.25 eq.), O-(benzotriazol-1-yl)-N,N,N',N'-tetramethyluronium tetrafluoroborate (838 mg, 1.25 eq.) and N,N-diisopropylethylamine (2.43 mL, 7 eq.) in N,N-dimethylformamide (9 mL) was stirred at room temperature for 20 h. The reaction mixture was partitioned between ethyl acetate and a saturated aqueous sodium hydrogencarbonate solution. The organic layer was separated and washed with water and brine, and dried over sodium sulfate, filtered and the solvents were removed in vacuo. The residue was purified by flash chromatography on silica gel with a 19:1:0 to 90:9:1 gradient of dichloromethane/methanol/ammonia as eluant, to afford 577 mg (57%) of the title compound as a light-yellow solid.

MS (m/z): 505.1 (M+H$^+$).

Intermediates a) 6-Chloro-5-(1-isopropyl-piperidin-4-yloxy)-1H-indole-2-carboxylic acid hydrochloride salt with 1 eq. lithium chloride A mixture of 6-chloro-5-(1-isopropyl-piperidin-4-yloxy)-1H-indole-2-carboxylic acid ethyl ester (2.55 g, 1.0 eq.) and lithium hydroxide monohydrate (352 mg, 1.2 eq.) in a mixture of tetrahydrofuran (24 mL), water (16 mL) and methanol (8 mL) was stirred at 80° C. for 5 h. The volatile components were reduced at a rotary evaporator and the remaining aqueous mixture was acidified (pH: 2) using hydrochloric acid 2N. The resulting mixture was dried in vacuo to afford 2.91 g (quant., 90% purity) of the title compound in form of light brown solid, which was used in the next step without further purification.

MS (m/z): 335.4 (M−H$^-$)

b) 6-Chloro-5-(1-isopropyl-piperidin-4-yloxy)-1H-indole-2-carboxylic acid ethyl ester To a cold (0° C.) mixture of 6-chloro-5-hydroxy-1H-indole-2-carboxylic acid ethyl ester (625 mg, 1.0 eq.), 1-Isopropyl-piperidin-4-ol (448 mg, 1.2 eq.) and triphenylphosphine (846 mg, 1.2 eq.) in tetrahydrofuran (8 mL) was added dropwise a solution of di-tert-butylazodicarboxylate (725 mg, 1.2 eq.) in tetrahydrofuran (7 mL). The reaction mixture was stirred for 20 h at room temperature. The volatile components were evaporated under reduced pressure and the residue was purified by flash chromatography on silica gel with a gradient of dichloromethane/methanol/ammonia from 98:2:0 to 90:9:1 as eluant to afford 635 mg (67%) of the tide compound as a light-yellow foam.

MS (m/z): 365.0 (M$^+$)

d) 6-Chloro-5-hydroxy-1H-indole-2-carboxylic acid ethyl ester

To a cooled (−78° C.) solution of 6-chloro-5-methoxy-1H-indole-2-carboxylic acid ethyl ester (930 mg, 1.0 eq.) in dichloromethane (20 mL), was slowly added a 1M solution of boron tribromide in dichloromethane (7.33 mL, 2.0 eq.). The mixture was stirred at room temperature for 1 h, partitioned between ethyl acetate and ice water. The aqueous layer was extracted with ethyl acetate and the combined organic fractions were washed with 10% sodium bicarbonate solution and brine, dried over sodium sulfate, filtered, evaporated to dryness and purified on silica gel, eluting with a 4:1 to 3:1 gradient of cyclohexane/ethyl acetate, to yield 655 mg (74%) of the title compound as a light-brown solid.

MS (m/e): 239.2 (M$^+$, 35%).

e) 6-Chloro-5-methoxy-1H-indole-2-carboxylic acid ethyl ester

Solution A: sodium nitrite (4.756 g, 1.12 eq) was added to a cold (0° C.) mixture of 3-chloro-p-anisidine (10 g, 1.0 eq) in concentrated hydrochloric acid (15.4 mL, 3.0 eq), water (20 mL) and ice (10 g). Sodium acetate (5.554 g, 1.1 eq) was added to adjust the pH to 3. Solution B: potassium hydroxide (4.417 g, 1.1 eq) was dissolved in water (5 mL) and added to a solution of ethyl-2-methylacetoacetate (9.6 mL, 1.1 eq) in ethanol (45 mL). Solution A was added to solution B at 0° C. and the mixture was stirred in the ice bath for 2 h, extracted with ethyl acetate, washed with a 10% sodium bicarbonate solution and brine, dried over sodium sulfate and concentrated in vacuo to yield 15.073 g of a red oil. The red oil was dissolved in 3 N hydrogen chloride in ethanol (223 mL, 14.0 eq) and stirred 3 h at reflux. The reaction mixture was partitioned between ethyl acetate and water. The aqueous layer was extracted twice with ethyl acetate and the combined organic fractions were washed with 10% sodium bicarbonate solution and brine, dried over sodium sulfate, filtered and concentrated in vacuo to afford 12.1 g of dark-brown oil.

The brown oil was dissolved in chloroform (100 mL) under nitrogen atmosphere and boron trifluoride ethyl etherate (5.61 mL, 1.0 eq) was added. The mixture was refluxed for 20 h, then partitioned between dichloromethane and 10% sodium bicarbonate solution. The aqueous layer was extracted twice with dichloromethane and the combined organic fractions were washed with 10% sodium bicarbonate solution and brine, dried over sodium sulfate, filtered, evaporated to dryness and purified by chromatography on silica gel, eluting with a 2:1 to 1:2 gradient of cyclohexane/dichloromethane, to yield 990 mg (6%) of the title compound as an orange solid.

MS (m/e): 253.1 (M$^+$, 70%).

Example 36

[6-Chloro-5-(1-isopropyl-piperidin-4-yloxy)-1H-indol-2-yl]-piperazin-1-yl-methanone To a cold (0° C.) solution of 4-[6-chloro-5-(1-isopropyl-piperidin-4-yloxy)-1H-indole-2-carbonyl]-piperazine-1-carboxylic acid tert-butyl ester (example 3, 547 mg, 1.0 eq.) in dichloromethane was added trifluoroacetic acid (1.23 mL, 10 eq.) dropwise. The reaction mixture was stirred 3 h at room temperature. The mixture was concentrated in vacuo and the residue was partitioned between ethyl acetate and a saturated aqueous sodium carbonate solution. The aqueous phase was extracted with ethyl acetate and the combined organic phases were dried over sodium sulfate, filtered and the solvents removed in vacuo. The residue was purified by flash chromatography on silica gel with a 90:9:1 dichloromethane/methanol/ammonia eluant to afford 413 mg (94%) of the title compound as a light-yellow solid.

MS (m/z): 405.4 (M+H$^+$).

Example 37

[6-Chloro-5-(1-isopropyl-piperidin-4-yloxy)-1H-indol-2-yl]-(4-cyclopropanecarbonyl-piperazin-1-yl)-methanone To a mixture of [6-chloro-5-(1-isopropyl-piperidin-4-yloxy)-1H-indol-2-yl]-piperazin-1-yl-methanone (example 36, 150 mg, 1.0 eq.) and cesium carbonate (243 mg, 2.0 eq.) in acetonitrile (8 mL) was added cyclopropane carbonylchloride. The reaction mixture was refluxed 4 h. The reaction mixture was concentrated in vacuo and the residue partitioned between tert-butylmethylether and water. The aqueous layer was extracted with tert-butylmethylether and the combined organic layers were washed with brine, dried over sodium sulfate, filtered and evaporated in vacuo. The residue was purified by flash chromatography on silica gel with a 98:2 to 95:5:0.25 gradient of dichloromethane/methanol/ammonia as eluant, to afford 59 mg (46%) of the title compound as a light-yellow solid.

MS (m/z): 473.4 (M+H$^+$).

Example 38

4-[6-Chloro-5-(1-isopropyl-piperidin-4-yloxy)-1H-indole-2-carbonyl]-piperazine-1-carboxylic acid dimethylamide The title compound was synthesized in analogy to example 37, from [6-chloro-5-(1-isopropyl-piperidin-4-yloxy)-1H-indol-2-yl]-piperazin-1-yl-methanone (example 36), and dimethylcarbamoyl chloride, to afford the title compound as a light-yellow solid (62%).

MS (m/z): 476.3 (M+H$^+$).

Example 39

[6-Chloro-5-(1-isopropyl-piperidin-4-yloxy)-1H-indol-2-yl]-(4-methanesulfonyl-piperazin-1-yl)-methanone The title compound was synthesized in analogy to example 37, from [6-chloro-5-(1-isopropyl-piperidin-4-yloxy)-1H-indol-2-yl]-piperazin-1-yl-methanone (example 36), and methanesulfonyl chloride, to afford the title compound as an off-white solid (72%).

MS (m/z): 483.4 (M+H$^+$).

Example 40

[1-Isopropyl-5-((1S,3R,5R)-8-isopropyl-8-aza-bicyclo[3.2.1]oct-3-yloxy)-1H-indol-2-yl]-[4-(4-trifluoromethyl-benzenesulfonyl)-piperazin-1-yl]-methanone A solution of (1R,3R,5S)-3-{1-isopropyl-2-[4-(4-trifluoromethyl-benzenesulfonyl)-piperazine-1-carbonyl]-1H-indol-5-yloxy}-8-aza-bicyclo[3.2.1]octane-8-carboxylic butyl ester (44 mg, 0.06 mmol) in ethyl acetate was treated with a 5M solution of hydrogen chloride in ethyl acetate. The solution was stirred overnight and evaporated to dryness. The residue was suspended in dichloromethane, and triethylamine (1.1 eq, 0.01 ml) added, followed by acetone (11 eq, 0.05 ml) and sodium triacetoxyborohydride (3 eq, 36 mg). The mixture was vigorously stirred 20 h at room temperature, the reaction quenched by addition of aqueous sodium hydrogencarbonate solution (2 ml). After 2 h, the mixture was diluted with water, and extracted twice with dichloromethane. The combined organic phases were washed with saturated aqueous sodium chloride solution, dried over magnesium sulfate and evaporated. The residue was purified by column chromatography on silica gel (1:0 to 8:1 toluene/methanol eluant) to afford the title compound as a light-yellow gum (9 mg, 24%). MS (m/z): 647.4 (M+H)$^+$.

Intermediates a) (1R,3r,5S)-3-{1-Isopropyl-2-[4-(4-trifluoromethyl-benzenesulfonyl)-piperazine-1-carbonyl]-1H-indol-5-yloxy}-8-aza-bicyclo[3.2.1]octane-8-carboxylic acid tert-butyl ester To a solution of (1R,3r,5S)-3-{2-[4-(4-trifluoromethyl-benzenesulfonyl)-piperazine-1-carbonyl]-1H -indol-5-yloxy}-8-aza-bicyclo[3.2.1]octane-8-carboxylic acid tert-butyl ester (109 mg, 0.16 mmol) in dry acetonitrile (3 ml) were added isopropyl methanesulfonate (2 eq, 45 mg) and caesium carbonate (2 eq, 107 mg). The mixture was heated 24 h at 95° C. (oil-bath temperature), cooled to room temperature and evaporated to dryness. The residue was suspended in water and extracted twice with ethyl acetate. The combined organic phases were washed with saturated aqueous sodium chloride solution, dried over magnesium sulfate and evaporated. The residue was purified by column chromatography on silica gel (1:0 to 9:1 dichloromethane/ethyl acetate eluant) to afford the title compound as a colorless solid (77 mg, 66%). MS (m/z): 705.3 (M+H)$^+$.

b) (1R,3R,5S)-3-{2-[4-(4-Trifluoromethyl-benzenesulfonyl)-piperazine-1-carbonyl]-1H-indol-5-yloxy}-8-aza-bicyclo[3.2.1]octane-8-carboxylic acid tert-butyl ester To a solution of 5-((1S,3R,5R)-8-tert-butoxycarbonyl-8-aza-bicyclo[3.2.1]oct-3-yloxy)-1H-indole-2-carboxylic acid (180 mg, 0.47 mmol) and 1-(4-trifluoromethyl-benzenesulfonyl)-piperazine hydrochloride (1.1 eq, 170 mg) in N,N-dimethylformamide (3.6 ml) was added triethylamine (1.2 eq, 0.056 ml). The mixture was stirred 5 min before the addition of N-hydroxybenzotriazole (0.24 eq, 15 mg) and N-(3-dimethylaminopropyl)-N'-ethyl-carbodiimide hydrochloride (1.1 eq, 98 mg). After overnight stirring, the solvent was evaporated under reduced pressure, the residue taken up in dichloromethane, and washed with sodium bicarbonate solution. The aqueous phase was extracted with dichloromethane, and the combined organic phases washed with water, half-saturated aqueous sodium chloride solution, dried over magnesium sulfate and evaporated. The residue was purified by column chromatography on silica gel (9:1 ethyl acetate/heptane eluant) to afford the title compound as an off-white solid (222 mg, 71%). MS (m/z): 677.1(M–H)$^-$.

c) 5-((1S,3R,5R)-8-tert-Butoxycarbonyl-8-aza-bicyclo[3.2.1]oct-3-yloxy)-1H-indole-2-carboxylic acid To a solution of 5-((1R,3r,5S)-8-tert-butoxycarbonyl-8-aza-bicyclo[3.2.1]oct-3-yloxy)-1H-indole-2-carboxylic acid ethyl ester (2.72 g, 7 mmol) in tetrahydrofuran (20 ml) was added a solution of lithium hydroxide monohydrate (1.2 eq, 330 mg) in water 5 ml). The mixture was heated 2 h at reflux. A further amount of 330 mg lithium hydroxide monohydrate was added and the mixture heated 2 h at reflux. Methanol was added to homogenize the mixture, and the mixture heated 4 h at reflux. The mixture was allowed to cool to room temperature, evaporated under reduced pressure and the residue partitioned between 1M aqueous potassium dihydrogenphosphate solution (200 ml) and ethyl acetate (200 ml). The phases were separated and the aqueous phase extracted with ethyl acetate (200 ml). The combined organic phases were dried over magnesium sulfate and evaporated under reduced pressure to afford the product as an off-white solid (2.34 g, 92%) that was used without further purification. MS (m/z): 385.2 (M–H)⁻.

d) 5-((1R,3R,5S)-8-tert-Butoxycarbonyl-8-aza-bicyclo[3.2.1]oct-3-yloxy)-1H-indole-2-carboxylic acid ethyl ester To a cooled (ice-bath) solution of ethyl 5-hydroxyindole-2-carboxylate (2.227 g, 11 mmol) (1R,3S,5S)-3-hydroxy-8-aza-bicyclo[3.2.1]octane-8-carboxylic acid tert-butyl ester (1 eq, 2.467 g) and triphenylphosphine (1.2 eq, 3.416 g) in tetrahydrofuran (50 ml), was added dropwise a solution of diethyl azodicarboxylate in tetrahydrofuran (10 ml). When the addition was complete, the mixture was slowly allowed to reach room temperature and stirred 1 week at room temperature. The solvent was evaporated under reduced pressure and the residue purified twice by column chromatography on silica gel (49:1 CHCl₃/tBuOMe eluant) to afford the product as an off-white solid (2.72 g, 60%). MS (m/z): 414.3 M⁺.

e) 1-(4-trifluoromethyl-benzenesulfonyl)-piperazine hydrochloride

To a solution of N-tert-butyloxycarbonylpiperazine (1.00 g, 5.37 mmol) in dichloromethane were added triethylamine (1.05 eq, 0.78 ml) and 4-(trifluoromethyl)-benzenesulfonyl chloride (1.02 eq, 1.345 g). The mixture was stirred overnight at room temperature, diluted with dichloromethane, washed with aqueous sodium bicarbonate solution, water, dried over magnesium sulfate and evaporated. The resulting white solid was dissolved in ethyl acetate and a 5 M solution of hydrogen chloride in ethyl acetate added dropwise. The mixture was stirred 3 h at 50° C. The precipitated solid was filtered and dried to afford the title compound (558 mg, 31%) which was used without further purification. MS (m/z): 295.4 (M+H)⁺.

Example 41

(4-Benzenesulfonyl-piperazin-1-yl)-[1-isopropyl-5-((1S,3r,5R)-8-isopropyl-8-aza-bicyclo[3.2.1]oct-3-yloxy)-1H-indol-2-yl]-methanone The title compound was prepared in analogy to example 40, from 5-((1S,3r,5R)-8-tert-butoxycarbonyl-8-aza-bicyclo[3.2.1]oct-3-yloxy)-1H-indole-2-carboxylic acid and 1-(phenylsulfonyl)-piperazine hydrochloride. Light-yellow gum. MS (m/z): 647.4 (M+H)⁺.

Example 42

[1-Isopropyl-5-((1S,3R,5R)-8-isopropyl-8-aza-bicyclo[3.2.1]oct-3-yloxy)-1H-indol-2-yl]-[4-(propane-2-sulfonyl)-pipcrazin-1-yl]-methanone The title compound was prepared in analogy to example 40, from 5-((1S,3r,5R)-8-tert-butoxycarbonyl-8-aza-bicyclo[3.2.1]oct-3-yloxy)-1H-indole-2-carboxylic acid and 1-(1-methylethylsulfonyl)piperazine. Light-yellow gum. MS (m/z): 545.5 (M+H)⁺.

Example 43

(4-Ethanesulfonyl-piperazin-1-yl)-[1-isopropyl-5-((1S,3r,5R)-8-isopropyl-8-aza-bicyclo[3.2.1]oct-3-yloxy)-1H-indol-2-yl]-methanone The title compound was prepared in analogy to example 40, from 5-((1S,3R,5R)-8-tert-butoxycarbonyl-8-aza-bicyclo[3.2.1]oct-3-yloxy)-1H-indole-2-carboxylic acid and 1-(ethylsulfonyl)-piperazine hydrochloride. Light brown foam. MS (m/z): 531.5 (M+H)⁺.

Example 44

[1-Isopropyl-5-((1S,3r,5R)-8-isopropyl-8-aza-bicyclo[3.2.1]oct-3-yloxy)-1H-indol-2-yl]-[4-(toluene-4-sulfonyl)-piperazin-1-yl]-methanone The title compound was prepared in analogy to example 40, from 5-((1S,3r,5R)-8-tert-butoxycarbonyl-8-aza-bicyclo[3.2.1]oct-3-yloxy)-1H-indole-2-carboxylic acid and 1-[(4-methylphenyl)sulfonyl]piperazine hydrochloride. Light-yellow gum. MS (m/z): 593.5 (M+H)⁺.

Example 45

[4-(4-Chloro-benzenesulfonyl)-piperazin-1-yl]-[5-((1S,3r,5R)-8-isopropyl-8-aza-bicyclo[3.2.1]oct-3-yloxy)-1H-indol-2-yl]-methanone The title compound was prepared in analogy to example 40, from 5-((1S,3r,5R)-8-tert-butoxycarbonyl-8-aza-bicyclo[3.2.1]oct-3-yloxy)-1H-indole-2-carboxylic acid and 1-[(4-chlorophenyl)sulfonyl]-piperazine hydrochloride. Off-white gum. MS (m/z): 571.5 (M+H)⁺.

Example 46

[1-Isopropyl-5-((1S,3R,5R)-8-isopropyl-8-aza-bicyclo[3.2.1]oct-3-yloxy)-1H-indol-2-yl]-[4-(4-methoxy-benzenesulfonyl)-piperazin-1-yl]-methanone The title compound was prepared in analogy to example 40, from 5-((1S,3r,5R)-8-tert-butoxycarbonyl-8-aza-bicyclo[3.2.1]oct-3-yloxy)-1H-indole-2-carboxylic acid and 1-[(4-methoxyphenyl)sulfonyl]-piperazine hydrochloride. Light-yellow gum. MS (m/z): 609.3 (M+H)⁺.

Example 47

[1-Isopropyl-5-((1S,3R,5R)-8-isopropyl-8-aza-bicyclo[3.2.1]oct-3-yloxy)-1H-indol-2-yl]-(4-phenylmethanesulfonyl-piperazin-1-yl)-methanone The title compound was prepared in analogy to example 40, from 5-((1S,3r,5R)-8-tert-butoxycarbonyl-8-aza-bicyclo[3.2.1]oct-3-yloxy)-1H-indole-2-carboxylic acid and 1-[(phenylmethyl)sulfonyl]-piperazine hydrochloride. Off-white gum. MS (m/z): 593.5 (M+H)⁺.

Example 48

4-{4-[1-Isopropyl-5-((1S,3R,5R)-8-isopropyl-8-aza-bicyclo[3.2.1]oct-3-yloxy)-1H-indole-2-carbonyl]-piperazine-1-sulfonyl}-benzonitrile The title compound was prepared in analogy to example 40, from 5-((1S,3R,5R)-8-tert-butoxycarbonyl-8-aza-bicyclo[3.2.1]oct-3-yloxy)-1H-indole-2-carboxylic acid and 1-[(4-cyanophenyl)sulfonyl]-piperazine hydrochloride. Light-yellow gum. MS (m/z): 604.3 (M+H)⁺.

Example 49

[1-(2,2-Difluoro-ethyl)-5-((1S,3R,5R)-8-isopropyl-8-aza-bicyclo[3.2.1]oct-3-yloxy)-1H-indol-2-yl]-(4-methanesulfonyl-piverazin-1-yl)-methanone The title compound was prepared in analogy to example 40, from 5-((1S,3R,5R)-8-tert-butoxycarbonyl-8-aza-bicyclo[3.2.1]oct-3-yloxy)-1H-indole-2-carboxylic acid and 1-(methylsulfonyl)-piperazine hydrochloride. Light-yellow gum. MS (m/z): 539.4 (M+H)$^+$.

Example 50

4-[5-(1-Isopropyl-piperidin-4-yloxy)-1H-indole-2-carbonyl]-piperazine-1-carboxylic acid tert-butyl ester The title compound was prepared in analogy to example 40b), from 5-[[1-(1-methylethyl)-4-piperidinyl]oxy]-1H-Indole-2-carboxylic acid and 1-(tert-butoxycarbonyl)piperazine. Light-yellow solid. MS (m/z): 471.1 (M+H)$^+$.

Example 51

[5-(1-Isopropyl-piperidin-4-yloxy)-1H-indol-2-yl]-(4-methanesulfonyl-piperazin-1-yl)-methanone To a solution of [5-(1-isopropyl-piperidin-4-yloxy)-1H-indol-2-yl]-piperazin-1-yl-methanone dihydrochloride (82 mg, 0.22 mmol) in dichloromethane (2 ml) were added triethylamine (4.2 eq, 0.13 ml) and methanesulfonyl chloride (1.4 eq, 0.02 ml). The mixture was stirred overnight, diluted with dichloromethane and washed with 1N aqueous sodium bicarbonate solution. The phases were separated, the aqueous phase extracted with dichloromethane, and the combined organic phases washed with brine and dried over magnesium sulfate. The crude product was purified by column chromatography on silica gel (1:0 to 5:1 dichloromethane/methanol eluant) to afford the title compound as an off-white solid. MS (m/z): 449.2 (M+H)$^+$.

Intermediate a) [5-(1-Isopropyl-piperidin-4-yloxy)-1H-indol-2-yl]-piperazin-1-yl-methanone dihydrochloride A solution of 4-[5-(1-isopropyl-piperidin-4-yloxy)-1H-indole-2-carbonyl]-piperazine-1-carboxylic acid tert-butyl ester (800 mg, 1.7 mmol) in ethyl acetate (25 ml) was treated with hydrogen chloride (5M in ethyl acetate, 12 ml) and the mixture stirred 72 h at room temperature. The resulting suspension was cooled to 0° C. (ice-bath), diethyl ether (2 ml) added and the mixture stirred 1 h. The precipitate was filtered and dried under vacuum to afford the title compound as an off-white solid. MS (m/z): 371.3 (M+H)$^+$.

Example 52

4-[1-Isopropyl-5-(1-isopropyl-piperidin-4-yloxy)-1H-indole-2-carbonyl]-piperazine-1-carboxylic acid tert-butyl ester The title compound was prepared in analogy to example 40a), from 4-[5-(1-isopropyl-piperidin-4-yloxy)-1H-indole-2-carbonyl]-piperazine-1-carboxylic acid tert-butyl ester and isopropyl methanesulfonate. Light-yellow foam. MS (m/z): 513.4 (M+H)$^+$.

Example 53

[1-Isopropyl-5-(1-isopropyl-piperidin-4-yloxy)-1H-indol-2-yl]-(4-methanesulfonyl-piperazin-1-yl)-methanone The title compound was prepared in analogy to example 51, from [1-isopropyl-5-(1-isopropyl-piperidin-4-yloxy)-1H-indol-2-yl]-piperazin-1-yl-methanone hydrochloride and methanesulfonyl chloride. Light-yellow foam. MS (m/z): 491.2 (M+H)$^+$.

Intermediate a) [1-Isopropyl-5-(1-isopropyl-piperidin-4-yloxy)-1H-indol-2-yl]-piperazin-1-yl-methanone hydrochloride The title compound was prepared in analogy to example 51a) from 4-[1-isopropyl-5-(1-isopropyl-piperidin-4-yloxy)-1H-indole-2-carbonyl]-piperazine-1-carboxylic acid tert-butyl ester. Light brown foam. MS (m/z): 413.2 (M+H)$^+$.

Example 54

4-[1-(2,2-Difluoro-ethyl)-5-(1-isopropyl-piperidin-4-yloxy)-1H-indole-2-carbonyl]-piperazine-1-carboxylic acid tert-butyl ester The title compound was prepared in analogy to example 40a), from 4-[5-(1-isopropyl-piperidin-4-yloxy)-1H-indole-2-carbonyl]-piperazine-1-carboxylic acid tert-butyl ester and 2,2-difluoroethyl trifluoromethanesulfonate. Off-white solid. MS (m/z): 535.5 (M+H)$^+$.

Example 55

[1-(2,2-Difluoro-ethyl)-5-(1-isopropyl-piperidin-4-yloxy)-1H-indol-2-yl]-(4-methanesulfonyl-piperazin-1-yl)-methanone The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and methanesulfonyl chloride. Light-yellow foam. MS (m/z): 513.4 (M+H)$^+$.

Intermediate a) [1-(2,2-Difluoro-ethyl)-5-(1-isopropyl-piperidin-4-yloxy)-1H-indol-2-yl]-piperazin-1-yl-methanone hydrochloride The title compound was prepared in analogy to example 51a) from 4-[1-(2,2-difluoro-ethyl)-5-(1-isopropyl-piperidin-4-yloxy)-1H-indole-2-carbonyl]-piperazine-1-carboxylic acid tert-butyl ester. White solid. MS (m/z): 435.3 (M+H)$^+$.

Example 56

1-{4-[1-Isopropyl-5-(1-isopropyl-piperidin-4-yloxy)-1H-indole-2-carbonyl]-piperazin-1-yl}-ethanone The title compound was prepared in analogy to example 51, from [1-isopropyl-5-(1-isopropyl-piperidin-4-yloxy)-

1H-indol-2-yl]-piperazin-1-yl-methanone hydrochloride and acetyl chloride. Light-yellow foam. MS (m/z): 455.5 (M+H)$^+$.

Example 57

[5-(1-Isopropyl-piperidin-4-yloxy)-1H-indol-2-yl]-[4-(2,2,2-trifluoro-ethanesulfonyl)-piperazin-1-yl]-methanone The title compound was prepared in analogy to example 51, from [5-(1-isopropyl-piperidin-4-yloxy)-1H-indol-2-yl]-piperazin-1-yl-methanone dihydrochloride and 2,2,2-trifluoro-ethanesulfonyl chloride. Off-white solid. MS (m/z): 517.3 (M+H)$^+$.

Example 58

(4-Cyclopropanecarbonyl-piperazin-1-yl)-[5-(1-isopropyl-piperidin-4-yloxy)-1H-indol-2-yl]-methanone The title compound was prepared in analogy to example 51, from [5-(1-isopropyl-piperidin-4-yloxy)-1H-indol-2-yl]-piperazin-1-yl-methanone dihydrochloride and cyclopropanoyl chloride. Light-yellow solid. MS (m/z): 439.5 (M+H)$^+$.

Example 59

4-[5-(1-Isopropyl-piperidin-4-yloxy)-1H-indole-2-carbonyl]-piperazine-1-carboxylic acid methyl ester The title compound was prepared in analogy to example 51, from [5-(1-isopropyl-piperidin-4-yloxy)-1H-indol-2-yl]-piperazin-1-yl-methanone dihydrochloride and methyl chloroformate. Light-yellow solid. MS (m/z): 429.3 (M+H)$^+$.

Example 60

4-[5-(1-Isopropyl-piperidin-4-yloxy)-1H-indole-2-carbonyl]-piperazine-1-carboxylic acid dimethylamide The title compound was prepared in analogy to example 51, from [5-(1-isopropyl-piperidin-4-yloxy)-1H-indol-2-yl]-piperazin-1-yl-methanone dihydrochloride and N,N-dimethylcarbamoyl chloride. Off-white solid. MS (m/z): 442.3 (M+H)$^+$.

Example 61

4-[5-(1-Isopropyl-piperidin-4-yloxy)-1H-indole-2-carbonyl]-piperazine-1-carboxylic acid diethylamide The title compound was prepared in analogy to example 51, from [5-(1-isopropyl-piperidin-4-yloxy)-1H-indol-2-yl]-piperazin-1-yl-methanone dihydrochloride and N,N-diethylcarbamoyl chloride. Off-white solid. MS (m/z): 470.6 (M+H)$^+$.

Example 62

[1-(2,2-Difluoro-ethyl)-5-(1-isopropyl-piperidin-4-yloxy)-1H-indol-2-yl]-[4-(propane-2-sulfonyl)-piperazin-1-yl]-methanone The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and 2-propanesulfonyl chloride. Light-yellow solid. MS (m/z): 541.3 (M+H)$^+$.

Example 63

(4-Cyclopropanecarbonyl-piperazin-1-yl)-[1-(2,2-difluoro-ethyl)-5-(1-isopropyl-piperidin-4-yloxy)-1H-indol-2-yl]-methanone The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and cyclopropanoyl chloride. Off-white solid. MS (m/z): 503.2 (M+H)$^+$.

Example 64

[1-(2,2-Difluoro-ethyl)-5-(1-isopropyl-piperidin-4-yloxy)-1H-indol-2-yl]-[4-(2,2,2-trifluoro-ethanesulfonyl)-piperazin-1-yl]-methanone The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and 2,2,2-trifluoro-ethanesulfonyl chloride. Light-yellow solid. MS (m/z): 581.3 (M+H)$^+$.

Example 65

4-[1-(2,2-Difluoro-ethyl)-5-(1-isopropyl-piperidin-4-yloxy)-1H-indol-2-carbonyl]-piperazine-1-carboxylic acid methyl ester The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and methyl chloroformate. Light-yellow solid. MS (m/z): 493.2 (M+H)$^+$.

Example 66

4-[1-(2,2-Difluoro-ethyl)-5-(1-isopropyl-piperidin-4-yloxy)-1H-indol-2-carbonyl]-piperazine-1-carboxylic acid dimethylamide The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and N,N-dimethylcarbamoyl chloride. Off-white solid. MS (m/z): 506.4 (M+H)$^+$.

Example 67

4-[1-(2,2-Difluoro-ethyl)-5-(1-isopropyl-piperidin-4-yloxy)-1H-indol-2-carbonyl]-piperazine-1-carboxylic acid diethylamide The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and N,N-diethylcarbamoyl chloride. Off-white solid. MS (m/z): 534.3 (M+H)$^+$.

Example 68

[1-(2,2-Difluoro-ethyl)-5-(1-isoprolpyl-piperidin-4-yloxy)-1H-indol-2-yl]-(4-trifluoromethanesulfonyl-piperazin-1-yl)-methanone The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and trifluoromethanesulfonyl chloride. Light-yellow solid. MS (m/z): 567.3 (M+H)⁺.

Example 69

4-[1-(2,2-Difluoro-ethyl)-5-(1-isopropyl-piperidin-4-yloxy)-1H-indole-2-carbonyl]-piperazine-1-sulfonic acid dimethylamide The title compound was prepared in analogy to example 51, from [1-(2,2-difluoro-ethyl)-5-(1-isopropyl-piperidin-4-yloxy)-1H-indol-2-yl]-piperazin-1-yl-methanone hydrochloride and dimethylsulfamoyl chloride. Light-yellow solid. MS (m/z): 542.3 (M+H)⁺.

Example 70

[1-Isopropyl-5-(1-isopropyl-piperidin-4-yloxy)-1H-indol-2-yl]-[4-(propane-2-sulfonyl)-piperazin-1-yl]-methanone The title compound was prepared in analogy to example 51, from [1-isopropyl-5-(1-isopropyl-piperidin-4-yloxy)-1H-indol-2-yl]-piperazin-1-yl-methanone hydrochloride and 2-propanesulfonyl chloride. Off-white solid. MS (m/z): 519.3 (M+H)⁺.

Example 71

(4-Cyclopropanecarbonyl-piperazin-1-yl)-[1-isopropyl-5-(1-isopropyl-piperidin-4-yloxy)-1H-indol-2-yl]-methanone The title compound was prepared in analogy to example 51, from [1-isopropyl-5-(1-isopropyl-piperidin-4-yloxy)-1H-indol-2-yl]-piperazin-1-yl-methanone hydrochloride and cyclopropanoyl chloride. Light-yellow solid. MS (m/z): 481.5 (M+H)⁺.

Example 72

[1-Isopropyl-5-(1-isopropyl-piperidin-4-yloxy)-1H-indol-2-yl]-[4-(2,2,2-trifluoro-ethanesulfonyl)-piperazin-1-yl]-methanone The title compound was prepared in analogy to example 51, from [1-isopropyl-5-(1-isopropyl-piperidin-4-yloxy)-1H-indol-2-yl]-piperazin-1-yl-methanone hydrochloride and 2,2,2-trifluoro-ethanesulfonyl chloride. Off-white solid. MS (m/z): 559.4 (M+H)⁺.

Example 73

4-[1-Isopropyl-5-(1-isopropyl-piperidin-4-yloxy)-1H-indole-2-carbonyl]-piperazine-1-carboxylic acid methyl ester The title compound was prepared in analogy to example 51, from [1-isopropyl-5-(1-isopropyl-piperidin-4-yloxy)-1H-indol-2-yl]-piperazin-1-yl-methanone hydrochloride and methyl chloroformate. Light-yellow solid. MS (m/z): 471.3 (M+H)⁺.

Example 74

4-[1-Isopropyl-5-(1-isopropyl-piperidin-4-yloxy)-1H-indole-2-carbonyl]-piperazine-1-carboxylic acid dimethylamide The title compound was prepared in analogy to example 51, from [1-isopropyl-5-(1-isopropyl-piperidin-4-yloxy)-1H-indol-2-yl]-piperazin-1-yl-methanone hydrochloride and N,N-dimethylcarbamoyl chloride. Off-white solid. MS (m/z): 484.4 (M+H)⁺.

Example 75

4-[1-Isopropyl-5-(1-isopropyl-piperidin-4-yloxy)-1H-indole-2-carbonyl]-piperazine-1-carboxylic acid diethylamide The title compound was prepared in analogy to example 51, from [1-isopropyl-5-(1-isopropyl-piperidin-4-yloxy)-1H-indol-2-yl]-piperazin-1-yl-methanone hydrochloride and N,N-diethylcarbamoyl chloride. Off-white solid. MS (m/z): 512.5 (M+H)⁺.

Example 76

[1-Isopropyl-5-(1-isopropyl-piperidin-4-yloxy)-1H-indol-2-yl]-(4-trifluoromethane-sulfonyl-piperazin-1-yl)-methanone The title compound was prepared in analogy to example 51, from [1-isopropyl-5-(1-isopropyl-piperidin-4-yloxy)-1H-indol-2-yl]-piperazin-1-yl-methanone hydrochloride and trifluoromethanesulfonyl chloride. Light-yellow solid. MS (m/z): 545.3 (M+H)⁺.

4-[1-Isopropyl-5-(1-isopropyl-piperidin-4-yloxy)-1H-indole-2-carbonyl]-piperazine-1-sulfonic acid dimethylamide The title compound was prepared in analogy to example 51, from [1-isopropyl-5-(1-isopropyl-piperidin-4-yloxy)-1H-indol-2-yl]-piperazin-1-yl-methanone hydrochloride and dimethylsulfamoyl chloride. Light-yellow foam. MS (m/z): 520.2 (M+H)⁺.

Example 78

4-{5-[1-(2,2,2-Trifluoro-ethyl)-piperidin-4-yloxy]-1H-indole-2-carbonyl}-piperazine-1-carboxylic acid methyl ester The title compound was prepared in analogy to example 40b), from 5-[1-(2,2,2-trifluoro-ethyl)-piperidin-4-yloxy]-1H-indole-2-carboxylic acid and methyl piperazine-1-carboxylate. Light yellow solid. MS (m/z): 469.3 (M+H)⁺.

Intermediates a) 5-[1-(2,2,2-trifluoro-ethyl)-piperidin-4-yloxy]-1H-indole-2-carboxylic acid The title compound was prepared in analogy to example 40c), from ethyl 5-[1-(2,2,2-trifluoro-ethyl)-piperidin-4-yloxy]-1H-indole-2-carboxylate. Light brown solid. MS (m/z): 343.1 (M+H)⁺.

b) Ethyl 5-[1-(2,2,2-trifluoro-ethyl)-piperidin-4-yloxy]-1H-indole-2-carboxylate The title compound was prepared in analogy to example 40d), from ethyl 5-hydroxyindole-2-carboxylate and 1-(2,2,2-trifluoro-ethyl)piperidin-4-ol, using diisopropyl azodicarboxylate instead of diethyl azodicarboxylate. Off-white solid. MS (m/z): 371.2 (M+H)⁺.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula I:

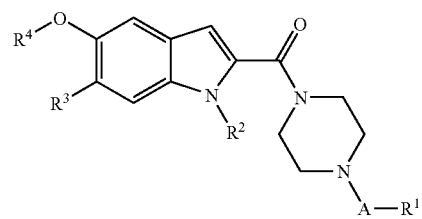

or any pharmaceutically acceptable salt thereof, wherein:
A is C(O) or S(O)$_2$;
R$^1$ is selected from the group consisting of:
 (1) lower alkyl,
 (2) lower alkoxy,
 (3) cycloalkyl, (4) lower cycloalkylalkyl,
(5) lower halogenalkyl,
(6) phenyl unsubstituted or substituted with one to three substituents independently selected from the group consisting of lower alkyl, lower alkoxy, halogen, lower halogenalkyl and cyano,
(7) lower phenylalkyl wherein the phenyl ring may be unsubstituted or substituted with one to three substituents independently selected from the group consisting of lower alkyl, lower alkoxy, halogen, lower halogenalkyl and cyano, and
(8) —NR$^5$R$^6$, wherein R$^5$ and R$^6$ independently from each other are selected from the group consisting of lower alkyl, cycloalkyl, lower cycloalkylalkyl, lower halogenalkyl and lower phenylalkyl, or alternatively, R$^5$ and R$^6$ together with the nitrogen atom to which they are attached form a 5- or 6-membered heterocyclic ring optionally containing a further heteroatom of nitrogen, oxygen or sulfur;

R$^2$ is selected from the group consisting of:
(1) hydrogen,
(2) lower alkyl,
(3) cycloalkyl,
(4) lower cycloalkylalkyl,
(5) lower hydroxyalkyl,
(6) lower alkoxyalkyl,
(7) lower halogenalkyl,
(8) lower cyanoalkyl,
(9) lower alkylsulfonyl,
(10) lower alkanoyl,
(11) phenylsulfonyl wherein the phenyl ring may be unsubstituted or substituted with one to three substitutents independently selected from the group consisting of lower alkyl, halogen, lower alkoxy, lower halogenalkoxy and lower hydroxyalkyl,
(12) phenyl unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino,
(13) benzodioxolyl,
(14) lower phenylalkyl, wherein the phenyl ring may be unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
(15) heteroaryl unsubstituted or substituted with one or two substituents independently selected from the group consisting of lower alkyl, lower alkoxy, cyano, morpholinyl and halogen;

R$^3$ is hydrogen, halogen or methyl; and
R$^4$ is either R$^{4a}$ or R$^{4b}$:

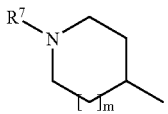

-continued

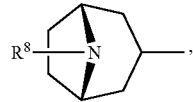

wherein:
m is 0 or 1;
R$^7$ is lower alkyl, cycloalkyl, or lower halogenalkyl; and
R$^8$ is lower alkyl, cycloalkyl, or lower halogenalkyl.

2. A compound of claim 1, wherein A is S(O)$_2$.
3. A compound of claim 1, wherein A is C(O).
4. A compound of claim 1, wherein R$^1$ is selected from the group consisting of:
(1) lower alkyl,
(2) lower alkoxy,
(3) cycloalkyl,
(4) lower cycloalkylalkyl,
(5) lower halogenalkyl,
(6) phenyl unsubstituted or substituted with one to three substitutents independently selected from the group consisting of lower alkyl, lower alkoxy, halogen, lower halogenalkyl and cyano, and
(7) lower phenylalkyl wherein the phenyl ring may be unsubstituted or substituted with one to three substituents independently selected from the group consisting of lower alkyl, lower alkoxy, halogen, lower halogenalkyl and cyano.

5. A compound of claim 1, wherein R$^1$ is selected from the group consisting of lower alkyl, cycloalkyl, lower cycloalkylalkyl and lower halogenalkyl.
6. A compound of claim 1, wherein R$^1$ is phenyl unsubstituted or substituted with one to three substituents independently selected from the group consisting of lower alkyl, lower alkoxy, halogen, lower halogenalkyl and cyano, or R$^1$ is lower phenylalkyl wherein the phenyl ring may be unsubstituted or substituted with one to three substituents independently selected from the group consisting of lower alkyl, lower alkoxy, halogen, lower halogenalkyl and cyano.
7. A compound of claim 1, wherein R$^1$ is —NR$^5$R$^6$, wherein R$^5$ and R$^6$ independently from each other are selected from the group consisting of lower alkyl, cycloalkyl, lower cycloalkylalkyl, lower halogenalkyl and lower phenylalkyl, or R$^5$ and R$^6$ together with the nitrogen atom to which they are attached form a 5- or 6-membered heterocyclic ring optionally containing a further heteroatom of nitrogen, oxygen or sulfur.
8. A compound of claim 1, wherein R$^1$ is lower alkoxy.
9. A compound of claim 1, wherein R$^2$ is selected from the group consisting of hydrogen, lower alkyl, cycloalkyl, lower cycloalkylalkyl, lower hydroxyalkyl, lower alkoxyalkyl, lower halogenalkyl, lower cyanoalkyl, and pyridyl wherein said pyridyl is unsubstituted or substituted with one or two substituents independently selected from the group consisting of lower alkyl, lower alkoxy, cyano, morpholinyl and halogen.
10. A compound of claim 1, wherein R$^2$ is hydrogen.
11. A compound of claim 1, wherein R$^2$ is lower alkyl.
12. A compound of claim 1, wherein R$^2$ is lower hydroxyalkyl or lower halogenalkyl.
13. A compound of claim 1, wherein R$^2$ is pyridyl which is unsubstituted or substituted with one or two substituents independently selected from the group consisting of lower alkyl, lower alkoxy, cyano, morpholinyl and halogen.

14. A compound of claim 1, wherein $R^3$ is halogen or methyl.

15. A compound of claim 1, wherein $R^4$ is

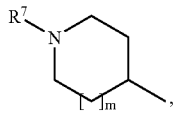

wherein $R^7$ is selected from the group consisting of lower alkyl, cycloalkyl and lower halogenalkyl; and m is 0 or 1.

16. A compound of claim 1, wherein $R^7$ is isopropyl or 2,2,2-trifluoroethyl.

17. A compound of claim 1, wherein m is 1.

18. A compound of claim 1, wherein $R^4$ is

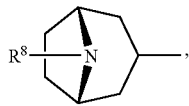

wherein $R^8$ is lower alkyl.

19. A compound of claim 1 selected from the group consisting of:
- [6-bromo-5-(1-isopropyl-piperidin-4-yloxy)-1H-indol-2-yl]-(4-methanesulfonyl-piperazin-1-yl)-methanone,
- [6-bromo-1-isopropyl-5-(1-isopropyl-piperidin-4-yloxy)-1H-indol-2-yl]-(4-methanesulfonyl-piperazin-1-yl)-methanone,
- [6-bromo-5-(1-isopropyl-piperidin-4-yloxy)-1H-indol-2-yl]-(4-ethanesulfonyl-piperazin-1-yl)-methanone,
- [6-bromo-1-isopropyl-5-(1-isopropyl-piperidin-4-yloxy)-1H-indol-2-yl]-(4-ethanesulfonyl-piperazin-1-yl)-methanone,
- [6-bromo-1-isopropyl-5-(1-isopropyl-piperidin-4-yloxy)-1H-indol-2-yl]-[4-(propane-2-sulfonyl)-piperazin-1-yl]-methanone, and any pharmaceutically acceptable salt thereof.

20. A compound of claim 1 selected from the group consisting of:
- [6-chloro-5-(1-isopropyl-piperidin-4-yloxy)-1H-indol-2-yl]-(4-methanesulfonyl-piperazin-1-yl)-methanone,
- [5-(1-isopropyl-piperidin-4-yloxy)-1H-indol-2-yl]-(4-methanesulfonyl-piperazin-1-yl)-methanone,
- [1-(2,2-difluoro-ethyl)-5-(1-isopropyl-piperidin-4-yloxy)-1H-indol-2-yl]-(4-methanesulfonyl-piperazin-1-yl)-methanone,
- (4-cyclopropanecarbonyl-piperazin-1-yl)-[1-(2,2-difluoro-ethyl)-5-(1-isopropyl-piperidin-4-yloxy)-1H-indol-2-yl]-methanone,
- 4-[1-(2,2-difluoro-ethyl)-5-(1-isopropyl-piperidin-4-yloxy)-1H-indole-2-carbonyl]-piperazine-1-carboxylic acid methyl ester,
- 4-[1-isopropyl-5-(1-isopropyl-piperidin-4-yloxy)-1H-indole-2-carbonyl]-piperazine-1-carboxylic acid methyl ester, and any pharmaceutically acceptable salt thereof.

21. A pharmaceutical composition comprising a comprising a therapeutically effective amount of a compound according to claim 1 and a pharmaceutically acceptable carrier.

22. A process for the manufacture of a compound of claim 1, which process comprises reacting a compound of the formula II

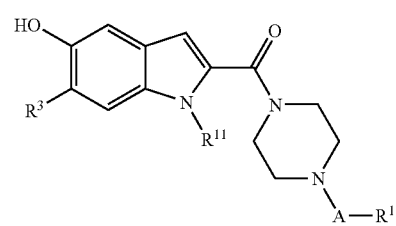

wherein $R^1$ and $R^3$ are as defined in claim 1, and $R^{II}$ is hydrogen or tert-butoxycarbonyl, with an alcohol of the formula III $$HO-R^4 \quad\quad III$$

wherein $R^4$ is as defined in claim 1,
in the presence of a trialkylphosphine or triphenylphosphine and of an azo compound to obtain a compound of the formula IA

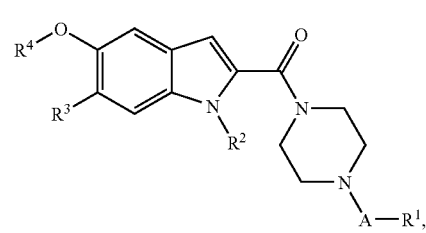

wherein $R^2$ is hydrogen,
and optionally converting the compound of formula IA into a compound of formula IB

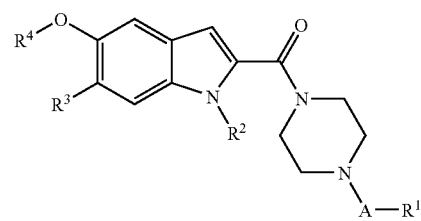

wherein $R^2$ is a group as defined in claim 1 other than hydrogen,
and optionally converting the compound obtained into a pharmaceutically acceptable salt.

* * * * *